(12) United States Patent
Sarver et al.

(10) Patent No.: US 8,876,290 B2
(45) Date of Patent: Nov. 4, 2014

(54) OBJECTIVE QUALITY METRIC FOR OCULAR WAVEFRONT MEASUREMENTS

(75) Inventors: Edwin Jay Sarver, Carbondale, IL (US); Thomas D. Padrick, Seattle, WA (US); Max Hall, Corona, CA (US)

(73) Assignee: Wavetec Vision Systems, Inc., Aliso Viejo, CA (US)

( * ) Notice: Subject to any disclaimer, the term of this patent is extended or adjusted under 35 U.S.C. 154(b) by 561 days.

(21) Appl. No.: 12/830,221

(22) Filed: Jul. 2, 2010

(65) Prior Publication Data

US 2011/0007270 A1    Jan. 13, 2011

Related U.S. Application Data

(60) Provisional application No. 61/228,120, filed on Jul. 23, 2009, provisional application No. 61/223,356, filed on Jul. 6, 2009.

(51) Int. Cl.
*A61B 3/14* (2006.01)
*A61B 3/10* (2006.01)

(52) U.S. Cl.
CPC .................................. *A61B 3/1015* (2013.01)
USPC ......................................................... 351/206

(58) Field of Classification Search
USPC ........................... 351/203, 205, 206, 210, 221
See application file for complete search history.

(56) References Cited

U.S. PATENT DOCUMENTS

| 4,019,813 | A | 4/1977 | Cornsweet et al. |
| 4,125,320 | A | 11/1978 | Rassow |
| 4,172,662 | A | 10/1979 | Vogel |
| 4,173,398 | A | 11/1979 | Okamoto et al. |
| 4,293,198 | A | 10/1981 | Kohayakawa et al. |
| 4,353,625 | A | 10/1982 | Nohda et al. |
| 4,372,655 | A | 2/1983 | Matsumura et al. |
| 4,376,573 | A | 3/1983 | Matsumura et al. |
| 4,390,255 | A | 6/1983 | Nohda et al. |
| 4,421,391 | A | 12/1983 | Matsumura et al. |
| 4,459,027 | A | 7/1984 | Kafri et al. |
| 4,541,697 | A | 9/1985 | Remijan |
| 4,640,596 | A | 2/1987 | Humphrey |
| 4,650,301 | A | 3/1987 | Humphrey |

(Continued)

FOREIGN PATENT DOCUMENTS

| AU | 2005234778 | 8/2011 |
| CA | 2515010 | 5/2013 |

(Continued)

OTHER PUBLICATIONS

"IOL Power Calculations Piggyback Lens," http://doctor-hill.com/iol-main/piggyback.html, accessed accessed on Feb. 24, 2010.

(Continued)

*Primary Examiner* — Mahidere Sahle
(74) *Attorney, Agent, or Firm* — Knobbe Martens Olson & Bear LLP

(57) ABSTRACT

A system and method for determining an objective quality metric for image data collected by a wavefront aberrometer. The method may include quantifying a plurality of characteristics of the image data and calculating the objective quality metric based on the quantified characteristics of the image data. The objective quality metric can be a weighted sum of the quantified characteristics of the image data. The weightings for the weighted sum can be determined based on subjective quality metrics assigned to a set of training image data by a human expert.

30 Claims, 11 Drawing Sheets

(56) References Cited

U.S. PATENT DOCUMENTS

| | | |
|---|---|---|
| 4,669,835 A | 6/1987 | Humphrey |
| 4,692,003 A | 9/1987 | Adachi et al. |
| 4,710,193 A | 12/1987 | Volk |
| 4,721,379 A | 1/1988 | L'Esperance |
| 4,730,917 A | 3/1988 | Krueger |
| 4,911,711 A | 3/1990 | Telfair et al. |
| 4,964,715 A | 10/1990 | Richards |
| 4,984,883 A | 1/1991 | Winocur |
| 4,995,716 A | 2/1991 | Warnicki et al. |
| 5,080,477 A | 1/1992 | Adachi |
| 5,144,478 A | 9/1992 | Toshimitsu |
| 5,157,427 A | 10/1992 | Humphrey |
| 5,164,750 A | 11/1992 | Adachi |
| 5,206,672 A | 4/1993 | Rowe |
| 5,208,619 A | 5/1993 | Campbell |
| 5,223,863 A | 6/1993 | Heine |
| 5,252,999 A | 10/1993 | Sukigara |
| 5,258,791 A | 11/1993 | Penny et al. |
| 5,270,749 A | 12/1993 | Okamura |
| 5,282,852 A | 2/1994 | Capetan et al. |
| 5,294,971 A | 3/1994 | Braunecker et al. |
| 5,307,097 A | 4/1994 | Baker |
| 5,329,322 A | 7/1994 | Yancey |
| 5,374,193 A | 12/1994 | Trachtman |
| 5,450,143 A | 9/1995 | Rowe et al. |
| 5,455,645 A | 10/1995 | Berger et al. |
| 5,493,109 A | 2/1996 | Wei et al. |
| 5,576,780 A | 11/1996 | Yancey |
| 5,777,719 A | 7/1998 | Williams et al. |
| 5,796,463 A | 8/1998 | Bullimore |
| 5,800,533 A | 9/1998 | Eggleston et al. |
| 5,861,937 A | 1/1999 | Fujieda |
| 5,909,268 A | 6/1999 | Isogai et al. |
| 5,936,706 A | 8/1999 | Takagi |
| 5,949,521 A | 9/1999 | Williams et al. |
| 5,963,300 A | 10/1999 | Horwitz |
| 5,968,094 A | 10/1999 | Werblin et al. |
| 5,968,095 A | 10/1999 | Norrby |
| 5,994,687 A | 11/1999 | Chanteloup et al. |
| 6,002,484 A | 12/1999 | Rozema et al. |
| 6,004,313 A | 12/1999 | Shimmick et al. |
| 6,007,204 A | 12/1999 | Fahrenkrug et al. |
| 6,042,232 A | 3/2000 | Luce et al. |
| 6,043,885 A | 3/2000 | Mazuet et al. |
| 6,050,687 A | 4/2000 | Bille et al. |
| 6,086,204 A | 7/2000 | Magnante |
| 6,095,651 A | 8/2000 | Williams et al. |
| 6,096,077 A | 8/2000 | Callahan et al. |
| 6,155,684 A | 12/2000 | Bille et al. |
| 6,199,986 B1 | 3/2001 | Williams et al. |
| 6,251,101 B1 | 6/2001 | Glockler |
| 6,262,328 B1 | 7/2001 | Wicks et al. |
| 6,264,328 B1 | 7/2001 | Williams et al. |
| 6,270,221 B1 | 8/2001 | Liang et al. |
| 6,271,915 B1 | 8/2001 | Frey et al. |
| 6,275,718 B1 | 8/2001 | Lempert |
| 6,299,311 B1 | 10/2001 | Williams et al. |
| 6,299,618 B1 | 10/2001 | Sugiura |
| 6,338,559 B1 | 1/2002 | Williams et al. |
| 6,379,005 B1 | 4/2002 | Williams et al. |
| 6,382,793 B1 | 5/2002 | Lai et al. |
| 6,382,794 B1 | 5/2002 | Lai et al. |
| 6,382,795 B1 | 5/2002 | Lai |
| 6,394,605 B1 | 5/2002 | Campin et al. |
| 6,409,345 B1 | 6/2002 | Molebny et al. |
| 6,419,671 B1 | 7/2002 | Lemberg |
| 6,439,720 B1 | 8/2002 | Graves et al. |
| 6,460,997 B1 | 10/2002 | Frey et al. |
| 6,497,483 B2 | 12/2002 | Frey et al. |
| 6,508,812 B1 | 1/2003 | Williams et al. |
| 6,550,917 B1 | 4/2003 | Neal et al. |
| 6,561,648 B2 | 5/2003 | Thomas |
| 6,570,143 B1 | 5/2003 | Neil et al. |
| 6,572,230 B2 | 6/2003 | Levine |
| 6,575,572 B2 | 6/2003 | Lai et al. |
| 6,578,963 B2 | 6/2003 | Pettit |
| 6,585,723 B1 | 7/2003 | Sumiya |
| 6,588,902 B2 | 7/2003 | Isogai |
| 6,598,975 B2 | 7/2003 | Liang et al. |
| 6,601,956 B1 | 8/2003 | Jean et al. |
| 6,609,793 B2 | 8/2003 | Norrby et al. |
| 6,609,794 B2 | 8/2003 | Levine |
| 6,626,535 B2 | 9/2003 | Altmann |
| 6,626,538 B1 | 9/2003 | Arrowsmith |
| 6,634,751 B2 | 10/2003 | Turner et al. |
| 6,637,884 B2 | 10/2003 | Martino |
| 6,658,282 B1 | 12/2003 | Eagan et al. |
| 6,679,606 B2 | 1/2004 | Campin et al. |
| 6,685,319 B2 | 2/2004 | Watson et al. |
| 6,702,806 B2 | 3/2004 | Gray et al. |
| 6,705,729 B2 | 3/2004 | Piers et al. |
| 6,724,464 B2 | 4/2004 | Yang et al. |
| 6,736,509 B2 | 5/2004 | Martino et al. |
| 6,736,510 B1 | 5/2004 | Van Heugten |
| 6,739,721 B2 | 5/2004 | Altmann |
| 6,761,454 B2 | 7/2004 | Lai et al. |
| 6,781,681 B2 | 8/2004 | Horwitz |
| 6,786,603 B2 | 9/2004 | Altmann |
| 6,793,654 B2 | 9/2004 | Lemberg |
| 6,819,413 B2 | 11/2004 | Neal et al. |
| 6,827,444 B2 | 12/2004 | Williams et al. |
| 6,836,374 B2 | 12/2004 | Esch et al. |
| 6,905,641 B2 | 6/2005 | Platt et al. |
| 6,908,196 B2 | 6/2005 | Herekar et al. |
| 6,926,710 B2 | 8/2005 | Cox et al. |
| 6,948,818 B2 | 9/2005 | Williams et al. |
| 6,997,555 B2 | 2/2006 | Dick et al. |
| 7,018,376 B2 | 3/2006 | Webb |
| 7,034,949 B2 | 4/2006 | Horwitz |
| 7,044,602 B2 | 5/2006 | Chernyak |
| 7,044,604 B1 | 5/2006 | Arrowsmith |
| 7,057,806 B2 | 6/2006 | Atkinson |
| 7,066,928 B2 | 6/2006 | Dick et al. |
| 7,068,439 B2 | 6/2006 | Esch et al. |
| 7,070,276 B2 | 7/2006 | Koretz |
| 7,077,522 B2 | 7/2006 | Williams |
| 7,111,938 B2 | 9/2006 | Andino et al. |
| 7,182,780 B2 | 2/2007 | Terwee et al. |
| 7,237,898 B1 | 7/2007 | Hohla et al. |
| 7,255,442 B2 | 8/2007 | Bucourt et al. |
| 7,303,281 B2 | 12/2007 | Wakil et al. |
| 7,336,371 B1 | 2/2008 | Haidner et al. |
| 7,341,348 B2 | 3/2008 | Eagan |
| 7,350,916 B2 | 4/2008 | Hong et al. |
| 7,350,920 B2 | 4/2008 | Levine |
| 7,357,509 B2 | 4/2008 | Williams et al. |
| 7,377,641 B2 | 5/2008 | Piers et al. |
| 7,380,942 B2 | 6/2008 | Molebny et al. |
| 7,401,919 B2 | 7/2008 | Vogelsang et al. |
| 7,406,263 B2 | 7/2008 | Graves et al. |
| 7,416,305 B2 | 8/2008 | Williams et al. |
| 7,425,067 B2 | 9/2008 | Warden et al. |
| 7,441,901 B2 | 10/2008 | Liang |
| 7,445,335 B2 | 11/2008 | Su et al. |
| 7,448,752 B2 | 11/2008 | Levine |
| 7,455,407 B2 | 11/2008 | Neal et al. |
| 7,461,938 B2 | 12/2008 | Lai |
| 7,467,869 B2 | 12/2008 | Kahlen |
| 7,475,989 B2 | 1/2009 | Campbell et al. |
| 7,476,248 B2 | 1/2009 | Harris et al. |
| 7,478,908 B2 | 1/2009 | Lai et al. |
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 | 9/2009 | Van Heugten |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,887,184 B2 | 2/2011 | Baer et al. |
| 7,988,291 B2 | 8/2011 | Ianchulev |
| 8,002,410 B2 | 8/2011 | Shea |

(56) References Cited

U.S. PATENT DOCUMENTS

| | | |
|---|---|---|
| 8,313,196 B2 | 11/2012 | Ianchulev |
| 8,333,474 B2 | 12/2012 | Michaels et al. |
| 8,394,083 B2 | 3/2013 | Van Heugten et al. |
| 8,475,439 B2 | 7/2013 | Van Heugten et al. |
| 8,545,023 B2 | 10/2013 | Holladay et al. |
| 8,550,624 B2 | 10/2013 | Padrick et al. |
| 2001/0041884 A1 | 11/2001 | Frey et al. |
| 2002/0016629 A1 | 2/2002 | Sandstedt et al. |
| 2002/0082629 A1 | 6/2002 | Cox et al. |
| 2002/0097376 A1* | 7/2002 | Applegate et al. ............ 351/205 |
| 2002/0105617 A1 | 8/2002 | Norrby et al. |
| 2002/0107567 A1 | 8/2002 | Terwee et al. |
| 2002/0118349 A1 | 8/2002 | Yang et al. |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1 | 1/2003 | Levine |
| 2003/0007127 A1 | 1/2003 | Levine |
| 2003/0009156 A1 | 1/2003 | Levine |
| 2003/0025080 A1 | 2/2003 | Sting et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0054358 A1 | 3/2004 | Cox et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0007603 A1 | 1/2005 | Arieli |
| 2005/0105044 A1 | 5/2005 | Warden et al. |
| 2005/0110946 A1* | 5/2005 | Youssefi et al. ............... 351/205 |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2006/0007395 A1 | 1/2006 | Mayo et al. |
| 2006/0007397 A1 | 1/2006 | Lai |
| 2006/0084956 A1 | 4/2006 | Sumiya |
| 2006/0126018 A1 | 6/2006 | Liang |
| 2006/0126019 A1 | 6/2006 | Liang et al. |
| 2006/0135952 A1 | 6/2006 | Curatu et al. |
| 2006/0174281 A1 | 8/2006 | Park |
| 2006/0203196 A1 | 9/2006 | Van Heugten |
| 2006/0203198 A1 | 9/2006 | Liang |
| 2006/0232744 A1 | 10/2006 | Liang |
| 2006/0279699 A1 | 12/2006 | Liang |
| 2007/0024808 A1 | 2/2007 | Campin et al. |
| 2007/0027442 A1 | 2/2007 | Campin et al. |
| 2007/0070292 A1 | 3/2007 | Liang |
| 2007/0115432 A1* | 5/2007 | Thibos ........................ 351/246 |
| 2007/0236702 A1 | 10/2007 | Neal et al. |
| 2007/0260157 A1 | 11/2007 | Norrby |
| 2008/0004610 A1 | 1/2008 | Miller et al. |
| 2008/0033546 A1 | 2/2008 | Liang |
| 2008/0084541 A1 | 4/2008 | Lai et al. |
| 2008/0088795 A1 | 4/2008 | Goldstein et al. |
| 2008/0159642 A1 | 7/2008 | Lyuboshenko |
| 2008/0231809 A1 | 9/2008 | Haigis |
| 2008/0278683 A1 | 11/2008 | Su et al. |
| 2008/0281304 A1 | 11/2008 | Campbell |
| 2008/0291396 A1 | 11/2008 | Baer et al. |
| 2009/0002628 A1 | 1/2009 | Williams et al. |
| 2009/0002631 A1 | 1/2009 | Campbell et al. |
| 2009/0009717 A1* | 1/2009 | Barrett et al. ................. 351/221 |
| 2009/0036980 A1 | 2/2009 | Norrby et al. |
| 2009/0048608 A1 | 2/2009 | Boukhny et al. |
| 2009/0096987 A1 | 4/2009 | Lai et al. |
| 2009/0103050 A1 | 4/2009 | Michaels |
| 2009/0109401 A1 | 4/2009 | Van Heugten |
| 2009/0164007 A1 | 6/2009 | Van Heugten |
| 2010/0030225 A1 | 2/2010 | Ianchulev |
| 2010/0036386 A1 | 2/2010 | Ianchulev |
| 2010/0042210 A1 | 2/2010 | Ianchulev |
| 2011/0001960 A1* | 1/2011 | Van Heugten ................ 356/121 |
| 2011/0015541 A1 | 1/2011 | Padrick |
| 2011/0267579 A1 | 11/2011 | Van Heugten |
| 2012/0147460 A1 | 6/2012 | Kubler |
| 2013/0021574 A1 | 1/2013 | Van Heugten |
| 2013/0070203 A1 | 3/2013 | Michaels |
| 2013/0131687 A1 | 5/2013 | Ianchulev |

FOREIGN PATENT DOCUMENTS

| | | |
|---|---|---|
| CN | 102497833 A | 6/2011 |
| DE | 43 10 561 A1 | 9/1994 |
| EP | 0931504 A1 | 7/1999 |
| EP | 2444021 | 4/2012 |
| EP | 2453822 | 5/2012 |
| EP | 2453823 | 5/2012 |
| EP | 1596710 | 1/2013 |
| GB | 1 209 451 | 10/1970 |
| IL | 138282 | 7/2004 |
| JP | 11-24434 | 5/1989 |
| JP | 9-122075 | 5/1997 |
| JP | 10-272100 | 10/1998 |
| JP | 2000-139996 | 5/2000 |
| JP | 2001-507258 A | 6/2001 |
| JP | 2001-314372 A | 11/2001 |
| JP | 2002-306418 A | 10/2002 |
| JP | 2003-509731 A | 3/2003 |
| JP | 2003-102689 A | 4/2003 |
| JP | 4972546 | 4/2012 |
| WO | WO 92/01417 | 2/1992 |
| WO | WO 96/22506 | 7/1996 |
| WO | WO 98/27863 | 7/1998 |
| WO | WO 01/06914 | 2/2001 |
| WO | WO 01/21061 A1 | 3/2001 |
| WO | WO 01/26591 A1 | 4/2001 |
| WO | WO 01/58339 | 8/2001 |
| WO | WO 02/17775 | 3/2002 |
| WO | WO 03/002047 | 1/2003 |
| WO | WO 03/039356 | 5/2003 |
| WO | WO 03/050472 A1 | 6/2003 |
| WO | WO 03/102498 A1 | 12/2003 |
| WO | WO 2004/093663 A2 | 11/2004 |
| WO | WO 2005/057252 | 6/2005 |
| WO | WO 2006/081031 A2 | 8/2006 |
| WO | WO 2009/086059 | 7/2009 |

OTHER PUBLICATIONS

"Refractive Vergence Formula Piggyback IOL Intraocular Lens Calculations," http://doctor-hill.com/iol-mail/piggyback.html, accessed on Feb. 12, 2010.

Aramberri, "Intraocular lens power calculation after corneal infrastructure surgery: Double-K method," J Cataract Refract Surg 29:2063-2068 (Nov. 2003).

Argento et al., "Intraocular lens power calculation after refractive surgery," J Cataract Refract Surg 29:1346-1351 (Jul. 2003).

Binkhorst RD., "Intraocular lens power calculation", Int Ophthalmol Clin. 1979 Winter; 19(4):237-52. (Abstract).

Binkhorst, "Power of the Pre-Pupillary Pseudoshakos," B.J.O. 56:332-37 (1972).

Binkhorst, "The Optical Design of the Intraocular Lens Implants," Opthalmic Surg 6(3): 17-31 (1975).

Brandser R., "Accuracy of IOL calculation in cataract surgery", Acta Ophthalmol Scand. Apr. 1997 75(2):162-5 (Abstract).

Chen et al., "Analysis of intraocular lens power calculationn in post-radial keratotomy eyes," J Cataract Refract Surg 29:65-? (Jan. 2003).

Colenbrander, "Calculation of the Power of an Iris-Clip Lens for Distance Vision," Br. J. Ophthal. 57:735-40(1973).

Cordonnier, M., et al., "How accurate is the hand-held refractor Retinomax(R) in measuring cycloplegic refraction: a further evaluation", Strabismus. Sep. 1998;6(3):133-I42 (Abstract).

(56) References Cited

OTHER PUBLICATIONS

Cua et al., Intraocular lens calculations in patients with corneal scarring and irregular astigmatism, J Cataract Refract Surg 29:1352-1357 (Jul. 2003).
Dalens H, Marcellier JJ, Moussiere L., "Use of the SRK (Sanders-Retzlaff-Kraft) regression formula in the preoperative calculation of the power of crystalline implants" (Abstract).
Donoso R., et al., "Emmetropization at cataract surgery. Looking for the best IOL power calculation formula according to the eye length", Arch Soc Esp Oftalmol. Sep. 2003;78(9):477-80 (Abstract).
El-Baha SM, et al., "Intraoperative biometry for intraocular lens (IOL) power calculation at silicone oil removal", Eur J Ophthalmol. Aug.-Sep. 2003;13(7):622-6. (Abstract).
El-Defrawy S., et al. "Evaluation of a hand-held autorefractor in children younger than 6", J Pediatr Ophthalmol Strabismus. ~ar-Apr. 1998;35(2):107-9 (Abstract).
Feiz, et al., "Intracular Lens Power Calculation After Laser In Situ Keratomileusis for Myopia and Hyperopia—A Standard Approach," Cornea 20(8):792-797 (2001).
Feordorov et al. "Estimation of Optical Power of the Intraocular Lens." Vestn. Onamol 80(4):27-31 (1967).
Filip M., et al. "Post-operatory biometry and refraction results estimated and refraction surprises—clinical study", Oftalmologia. 2003;56(1):11-4 (Abstract).
Gernet, "IOL Calculation According to Gernet and the GOW70 PC Programme," Abstract from Ophthalmologe 98:873-876 (2001).
Gimbel et al., "Accuracy and Predictability of Intraocular Lens Power Calculation After Laser In Situ Keratomileusis," J Cataract Refract Surg 27:571-576 (Apr. 2001).
Gimbel et al., "Accuracy and Predictability of Intraocular Lens Power Calculation After photorefractive keratectomy," J Cataract Refract Surg 26:1147-1151 (Apr. 2000).
Gupta, et al., *"Design and use of an infrared Pupilometer for real-time pupil mapping in response to incremental illumination levels,"*2000 Optical Society of America, Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/Refractive+Surgery+Feature/Aberrometer-aims-to-improve-refractive-cataract-ou/Article Standard/Article/detail/559856.
Hamilton et al., "Cataract Surgery in Patients with Prior Refractive Surgery", Current Opinion in Ophthalmology 14:44-53 (2003).
Happe W. et al., "Intraoperative Skiaskopie zur Bestimmung des Brechwerts einer zu implantierenden Intraokularlinse" [Intraoperative retinoscopy for determining the refractice value of an implantable intraocular lens] Klin. Monatsbl. Augenheilkd. vol. 210, No. 4, 1997, pp. 207-212.
Harvey et al., "Reproducability and accuracy of measurements with a hand held autorefractive in children," Journal of Opthalmology 81:941-948 (1997).
Hoffer KJ, et al., "A simple lens power calculation program for the HP-67 and HP-97 Calculators", JAm Intraocul Implant Soc. Oct. 1978; 4(4):197-9. (Abstract).
Hoffer, "Calculating Corneal Power After Refractive Surgery," Cataract & Refractive Surgery Today 4(4):23-25 (Apr. 2004).
Hoffer, "Mathematics and computers in intraocular lens calculation," Am Intra-Ocular Implant Soc. J. 1(1):4-5 (1975).
Holladay, et al., "A three-part system for refining intraocular lens power calculations," Cataract Refract Surg. 14:17-24 (Jan. 1988).
Holladay, Jack T., "Refractive Power Calculations for Intraocular Lenses in Phakic Eye," American Journal of Ophthalmology, Jul. 1993, pp. 63-66.
Holladay, JT et al., Refining Toric Soft Contact Lens Prescriptions, CLAO J. 1984, 10:326-31.
Holladay, JT, et al. "Calculating the Surgically Induced Refractive Change Following Ocular Surgery", J. Cataract Refract. Surg. 1992; 18:429-43.
Hunt et al., "Evaluation of the measurement of refractive error by the PowerRefractor: a remote, continuous and binocular measurement system of oculomotor function," Br. J. Opthalmol 87:1504-1508 (2003).
Ianchulev, "Method for Intraoperative Refractive IOL Calculation," Poster Presentation at Ophthalmology Conference (Apr. 2004).
Ianchulev, et al. (Aug. 2005), "Intraoperative optical refractive biometry for intraocular lens power estimation without axial length and keratometry measurements," Journal of Cataract & Refractive Surgeq, vol. 31, Issue 8, pp. 1530-1536, Abstract.
Isenberg et al., "Use of the HARK Autorefractor in Children," American Journal of Ophthalmology 131(4):438-441 (2001).
luorno JD, et al., "Clinical comparison of the Welch Allyn SureSight handheld auto refractor versus cycloplegic auto refraction and retinoscopic refraction", J AAPOS. Apr. 2004;8(2):123-7 (Abstract).
Ivanov MN, et al., "Formula for calculating the IOL focal power", Vestn Oftalmol. Jul.-Aug. 2003;119 (4):52-4 (Abstract).
Iwami S et al., "Prediction of Postoperative Refraction Using Intraoperative Retinoscopy" Journal of Japanese Ophthalmological Society, vol. 103, No. 7, 1999, pp. 551-555.
Koo, So, et al., "Comparison of IOL powers by corrected method in eyes after PRK and LASIK", Korean J Ophthalmol. Jun. 2002;16(1):26-31 (Abstract).
Kora et al., "Intraocular lens power calculation for lens exchange," J Cataract Surg 27:543-548 (Apr. 2001).
Liang, et al. "Comparison of the handheld Retinomax K-Plus 2 and on-table autokeratometers in children with and without cycloplegia," J Cataract Refract Surg 30:670-674 (Mar. 2004).
Liang, et al. "Aberrations and Retinal Image Quality of the Normal Human Eye", J. Optical Society of America, vol. 14, No. 11, Nov. 1997.
Liang. et al. "Comparison of Measurements of Refractive Errors Between the Hand-held Retinomax and On-table Autorefractors in Cyclopleged and Noncyclopleged Children," American Journal of Ophthalmology 136(6): 1120-1128 (Dec. 2003).
Lipatov DV., "Assessment of the efficiency of different formulae applied to calculating the optic power of an intraocular lens in transscleral fixation", Vestn Oftalmol, Nov.-Dec. 2003; 119(6):33-5 (Abstract).
Ma, et al., "Simple method for accurate alignment in toric phakic and aphakic intraocular lens implantation," J Cataract Refract Surg, Technique, Oct. 2008, vol. 34, pp. 1631-1636.
Mackool RJ., "The cataract extraction-refraction-implantation technique for IOL power calculation in difficult cases", J Cataract Refract Surg. Apr. 1998;24(4):434-5 (Abstract).
Masket, et al., "Atlas of Cataract Surgery," Book cover in 1 page, Front Matter in 11 pages (Table of Contents in 3 pages), Chapter 19 pp. 147-158, Published by Martin Dunitz Ltd 1999, United Kingdom.
Methling D, Kalb G., "A New Program for Calculating Intraocular Lenses", Klin Monatsbl Augenheilkd. Oct. 1992:201 (4):247-53 (Abstract).
Moreno-Barriuso, et al., "Laser Ray Tracing Versus Hartmann-Shack Sensor for Measuring Optical Aberrations in the Human Eye", J. Optical Society of America, vol. 17. No. 6, Jun. 2000.
Nemeth et al., "Optical and ultrasound measurement of axial length and anterior chamber depth for intraocular lens power calculation," J Cataract Refract Surg 29:85-88 (Jan. 2003).
Olsen, "Theoretical approach to intraocular lens calculation using Gaussian optics," J Cataract Refract Surg 13:141-145 (Mar. 1987).
Olsen, "Theoretical computer-assisted prediction versus SRK prediction of postoperative refraction after intraocular lens implantation," J Cataract Refract Surg 13:141-145 (Mar. 1987).
Orr et al., "Manifest Refraction Versus Autorefraction for Patients with Subfoveal Choroidal Neovascularization," Investigative Ophthalmology & Visual Science 42(2): 447-451 (Feb. 2001).
Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).
Photograph of Oculus Instrument, accessed at http://www.oculus.de/en/sites/popup_bild_gross.php?news=&id=1056 on Apr. 29, 2011.
Quiroga. et al., *"Fourier transform method for automatic processing of moire deflectograms,"* Jun. 1999, Society of Photo-Optical Instrumentation Engineers, pp. 974-982.

(56) References Cited

OTHER PUBLICATIONS

Raj et al., "Clinical evaluation of automated refractio in anterior chamber pseudophakia," British Journal of Ophthalmology 75:42-44 (1991).

Raj et al., "Objective autorefraction in posterior chamber pseudophakia," British Journal of Ophthalmology 74:731-733 (1990).

Raj PS, et al., "Comparative evaluation of the Allergan Humphrey 570 and Canon RK-I autorefractors: I. Objective autorefraction in normal subjects", Eye. 1992;6 (Pt 3):284-6 (Abstract).

Retzlaff J., "A new intraocular lens calculation formula", J Am Intraocul Implant Soc. Apr. 1980 6(2):148-52. (Abstract).

Rubin A., et al., "Refractive variation during autorefraction: multivariate distribution of refractive status", Optom Vis Sci. Jun. 1995;72(6):403-10 (Abstract).

Rubin A., et al., "Variation during autorefraction: influence of two different target types", Ophthalmic Physiol Opt. Jan. 1997;17(1):38-43 (Abstract).

Sanders et al., "Comparison of the SRK/T formula and other theoretical and regression formulas," J Cataract Refract Surg. 16:341-346 (May 1990).

Sanders et al., "Comparisons of the SRK™ formula and other second generation formulas," J Cataract Refract Surg 14;136-141 (Mar. 1988).

Senjo, et al., "Prediction of Postoperative Refraction Using Intraoperative Retinoscopy," Journal of Japanese Ophthalmological Society, 1999, vol. 103, No. 7, pp. 551-555, Abstract.

Siahmed K., et al., "Optic biometry in intraocular lense calculation for cataract surgery. Comparison with usual methods", J Fr Ophthalmol. Nov. 2001:24(9):922-6 (Abstract).

Siganos et al., "Autorefractometry after laser in situ keratomileusis," J Cataract Refract Surg 29.133-137 (Jan. 2003).

Steele, G., et al., "Cycloplegic auto refraction results in pre-school children using the Nikon Retinomax Plus and the Welch Allyn SureSight", Optom Vis Sci. Aug. 2003;80(8):573-7 (Abstract).

Straub et al., "*Design of a compact Shack-Hartmann aberrometr for real-time measurement of aberrations in human eyes*," 2000 Optical Society of America, pp. 110-113.

Suto et al., "Adjusting intraocular lens power for sulcus fixation," J Cataract Refract Surg 29:1913-1917 (Oct. 2003).

Thall et al., "Linear Regression Software for Intraocular Lens Implant Power Calculation," American Journal of Ophthalmology 101:597-599 (May 1986).

Thijssen JM., "The emmetropic and the iseikonic implant lens: computer calculation of the' refractive power and its accuracy", Ophthalmologica. 1975;171 (6):467-86 (Abstract).

Thompson et al., "A New Posterior Chamber Intraocular Lens Formula for Axial Myopes," Ophthalmology 91(5): 484-488 (May 1984).

Tromans et al., "Accuracy of intraocular lens power calculation in paediatric cataract surgery," Br J Ophthalmol 85:939-941 (2001).

Tseng, et al., "Calculating the optimal rotation of a misaligned toric intraocular lens," J Catactact Refract Surg. Laboratory Science, Oct. 2008, vol. 34, pp. 1767-1772.

Villada Jr., et al., "Comparative evaluation of the Allergan Humphrey 570 and Canon RK-I autorefractors: II, Objective autorefraction in pseudophakes", Eye. 1992;6 (Pt 3):287-9 (Abstract).

Van Heugten, T., et al. "Validation of Novel Hartmann-Moire Wavefront Sensor with Large Dynamic Range", presented at Wavefront Congress, Feb. 17, 2008, available at http://www.wavefront-congress.org/info/listing_detail.asp?absID-12, last visited Feb. 28, 2008.

Walline Jj, "Repeatability and validity of astigmatism measurements", J Refract Surg. Jan.-Feb. 1999; 15(1):23-31 (Abstract).

Wiechens, et al., "Bilateral Cataract after Phakic Posterior Chamber Top Hat-style Silicone Intraocular Lens," Journal of Refractive Surgery, Jul./Aug. 1997; vol. 13, No. 4, Cover and Table of Contents in 2 pages, pp. 392-397.

Wood IC., "A review of autorefractors", Eye. 1987;1 (Pt 4):529-35 (Abstract).

Yalvac IS, et al., "Calculation of intraocular lens power with the SRK IIformula for axial high myopia" Eur J Ophthalmol. Oct.-Dec. 1996;6(4):375-8 (Abstract).

Zaldivar et al., "Intraocular lens power calculations in patients with extreme myopia." J Cataract Refract Surg 26:668-674 (May 2000).

Rosales et al., "Phakometry and lens tilt and decentration using a custom-developed Purkinje imaging apparatus: validation and measurements," Journal of the Optical Society of America, vol. 23, No. 3, Mar. 2006, pp. 509-520.

Castro et al., "Tilt and decentration of intraocular lenses in vivo from Purkinje and Scheimpflug imaging: Validation study," J. Cataract Refract. Surg. 2007; 33:418-429.

Tabernero et al., "Instrument for measuring the misalignments of ocular surfaces," Optical Society of America, Oct. 30, 2006, vol. 14, No. 22.

Uozato et al., "Intraoperative Confirmation Device for IOL Centering," Folia Ophthalmologica Japonica, vol. 41, 1990, pp. 1325-1329.

* cited by examiner

OBJECTIVE QUALITY METRIC FOR OCULAR WAVEFRONT MEASUREMENTS

CROSS-REFERENCE TO RELATED APPLICATIONS

This application claims priority to the following United States provisional patent applications, each of which is hereby incorporated herein by reference in its entirety to be considered part of this specification: U.S. Provisional Patent Application 61/223,356, filed Jul. 6, 2009, and entitled "OBJECTIVE QUALITY METRIC FOR OCULAR WAVEFRONT MEASUREMENTS"; and U.S. Provisional Patent Application 61/228,120, filed Jul. 23, 2009, and entitled "OBJECTIVE QUALITY METRIC FOR OCULAR WAVEFRONT MEASUREMENTS."

BACKGROUND OF THE INVENTION

1. Field of the Invention

The field of the invention relates to ophthalmic equipment and methods. In particular, the field of the invention relates to the analysis of image data collected by wavefront aberrometers.

2. Description of the Related Art

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple spherical and cylindrical errors that cause myopia, hyperopia, or regular astigmatism, to more complex refractive errors that can cause, for example, halos and starbursts in a person's vision.

Many interventions have been developed over the years to correct various ocular aberrations. These include spectacles, contact lenses, corneal refractive surgery, such as LASIK or corneal implants, and intraocular lenses (IOLs). The diagnosis and specification of sphero-cylindrical spectacles and contact lenses for treatment of myopia, hyperopia, and astigmatism are well-established. Some surgery-based techniques are not as predictable as may be desired but are still in widespread use and can yield good corrective results.

A wavefront aberrometer is an ophthalmic instrument capable of measuring ocular aberrations. These include low-order aberrations like defocus and the magnitude and axis of regular astigmatism. These low-order ocular aberrations can be quantified by, for example, second-order Zernike polynomials. In addition, wavefront aberrometers may also be capable of measuring higher-order aberrations of the patient's vision. These higher-order aberrations can be quantified by, for example, third-order, or higher, Zernike polynomials. These instruments can provide the theoretical information required to improve vision correction beyond the lower-order aberrations of defocus and regular astigmatism, such as, for example, in a LASIK procedure. However, wavefront aberrometers are also useful in diagnosing and prescribing spectacles, contact lenses, and IOLs, which typically correct sphero-cylindrical aberrations.

Several different types of wavefront aberrometers are known. These include Shack-Hartmann wavefront aberrometers and Talbot-Moiré wavefront aberrometers, among others. A Shack-Hartmann wavefront aberrometer operates by injecting a probe beam of laser light into the eye of a patient. The probe beam scatters from the retina back towards the instrument. The optical wavefronts of the scattered beam are aberrated by the patient's eye. After emerging from the eye, the scattered beam is collected and transmitted to an array of lenslets. The lenslets sample the beam at different spatial locations and focus it onto a detector in the form of an array of spots. If the scattered beam consists of planar wavefronts, then the array of spots focused on to the detector by the lenslets are regularly spaced. However, aberrated wavefronts cause each of the spots to be displaced in a manner that depends upon the local curvature of the wavefronts at the spatial location of each lenslet. An image of the spot pattern can be analyzed to determine the refractive properties of the patient's eye.

A Talbot-Moiré wavefront aberrometer also projects a probe beam of laser light into the eye of a patient. After the probe beam scatters from the retina, the scattered beam is collected and transmitted to one or more reticles, such as Ronchi grids. In one design, when the Ronchi grids are separated by a Talbot distance and are rotated with respect to one another, a Moiré fringe pattern is created, which can be imaged by a camera. An image of the Moiré fringe pattern can be analyzed to determine the refractive properties of a patient's eye.

SUMMARY OF THE INVENTION

In some embodiments, in a wavefront aberrometer system, a method comprises: obtaining one or more images that are indicative of a patient's ocular aberrations; determining a plurality of characteristics of the one or more images; determining one or more objective quality metrics for the one or more images, the one or more objective quality metrics being based on an aggregate of the plurality of characteristics of the one or more images; selecting at least a portion of the one or more images based on the one or more objective quality metrics; and determining one or more ocular aberration measurements using the selected portion of the one or more images.

In some embodiments, an ophthalmic device comprises: a wavefront aberrometer; and a processing module communicatively coupled to the wavefront aberrometer, the processing module being programmed to perform a method comprising, obtaining one or more images that are indicative of a patient's ocular aberrations; determining a plurality of characteristics of the one or more images; determining one or more objective quality metrics for the one or more images, the one or more objective quality metrics being based on an aggregate of the plurality of characteristics of the one or more images; selecting at least a portion of the one or more images based on the one or more objective quality metrics; and determining one or more ocular aberration measurements using the selected portion of the one or more images.

In some embodiments, a computer readable medium comprises instructions that, when read by a computer, cause the computer to perform a method that comprises: obtaining one or more images that are indicative of a patient's ocular aberrations; determining a plurality of characteristics of the one or more images; determining one or more objective quality metrics for the one or more images, the one or more objective quality metrics being based on an aggregate of the plurality of characteristics of the one or more images; selecting at least a portion of the one or more images based on the one or more objective quality metrics; and determining one or more ocular aberration measurements using the selected portion of the one or more images.

BRIEF DESCRIPTION OF THE DRAWINGS

For purposes of summarizing the disclosure, certain aspects, advantages and features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein. Certain embodiments are schematically illustrated in the accompanying drawings, which are for illustrative purposes only.

DETAILED DESCRIPTION OF THE PREFERRED EMBODIMENT

Figure 1:
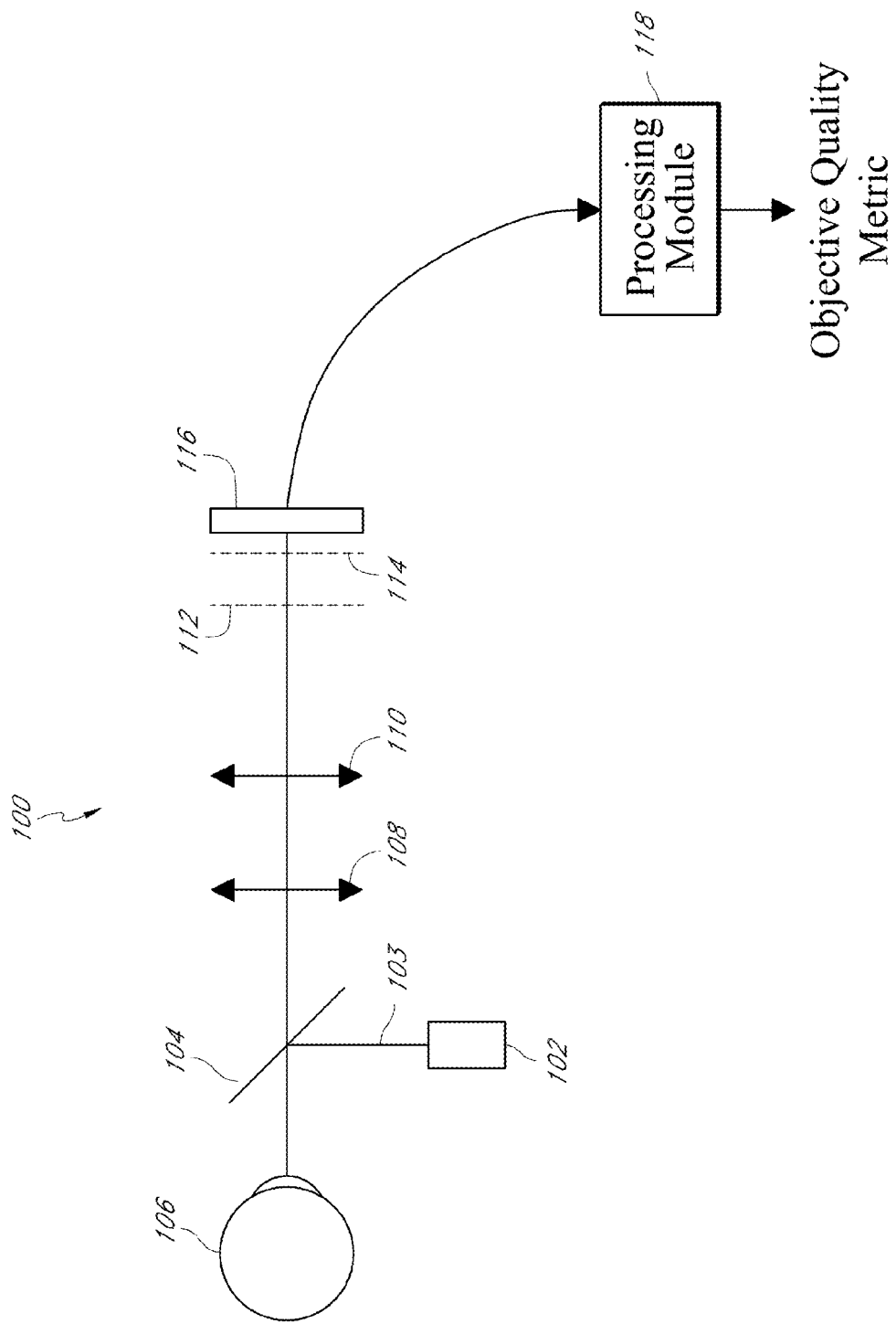
FIG. 1 is a schematic diagram of an example wavefront aberrometer capable of producing images that are indicative of ocular aberrations.

As already discussed, there are a number of different types of wavefront aberrometers that collect image data that is indicative of the ocular aberrations of a patient's eye. This image data can be analyzed by a computer to qualitatively or quantitatively determine the optical aberrations exhibited by the eye. Regardless of the type of wavefront aberrometer that is used in an ophthalmic application to obtain image data that is indicative of ocular aberrations, the accuracy, precision, and reliability of the refractive measurements of the eye that are made by analyzing the image data typically depend, at least in part, upon the quality of the image data.

The quality of wavefront aberrometer image data can be compromised in a number of ways, thus leading to suboptimal results in the ocular aberration measurements obtained from the aberrometer image data. For example, several factors that affect the quality of wavefront aberrometer image data include the state of alignment of the aberrometer with the eye, the presence of ambient light in wavelength ranges where the aberrometer operates, the moistness of the surface of the cornea of the patient's eye, patient movement during collection of image data, clouding of the natural crystalline lens (in the case of a phakic refractive power measurement), air bubbles, indispersed viscoelastic material in the eye, hardware implementation, image processing algorithms, calibration etc.

The various factors that affect the quality of wavefront aberrometer image data can be somewhat unpredictable, which can also lead to uncertainty in the measurements that are derived from the image data. Therefore, there is a need for ophthalmic equipment and techniques capable of increasing the reliability of wavefront aberrometer measurements. Typically, as the quality of the image data improves, the reliability and accuracy of the ocular aberration measurements also improve. Thus, as described herein, it would be desirable to be able to objectively determine the quality of collected wavefront image data so as to be able to judge whether, and to what extent, to use a particular set of collected wavefront image data in the determination of ocular aberration measurements.

Given the capability to accurately and reliably judge the quality of the wavefront aberrometer image data, image data that is judged to be acceptable can be used in the determination of refractive power measurements, while image data that is judged to be unacceptable can be discarded or otherwise play an attenuated role in the determination of refractive power measurements. In this way, the probability that high quality ocular wavefront aberration measurements are reported by the aberrometer could be increased.

In some embodiments, a method for analyzing wavefront aberrometer image data involves the usage of a set of functions (e.g., scalar functions) and/or image processing techniques which operate on captured wavefront aberrometer image data, whether it is a single image or multiple images and whether the image data is raw or preprocessed. The outputs of each of these functions can be weighted by a set of coefficients and then combined to provide an objective quality metric (e.g., a quantitative score) which represents the overall quality of the wavefront aberrometer image data. In some embodiments, the coefficients used in an exam quality calculation are determined using a test set of data. For example, given a test set of images, the coefficients used in an exam quality calculation can be set so as to reduce the error between one or more subjective quality metrics provided by a human expert for the test set of images and one or more corresponding objective quality metrics determined from the test set of images.

In some embodiments, the equipment and techniques described herein can be used to improve the reliability of analysis of fringe pattern images from a Talbot-Moiré wavefront aberrometer by objectively quantifying the quality of collected image data. The objective exam quality metric can be used to increase reliance upon wavefront aberrometer image data that is found to be of higher quality while decreasing reliance upon image data that is found to be of lower quality or to be otherwise unreliable. This increased reliance upon wavefront aberrometer image data of higher quality can lead to more accurate refractive power measurements, which are derived from the wavefront aberrometer image data. The techniques described herein can also be adapted to provide objective exam quality metrics for images from other types of wavefront aberrometers, including, for example, Shack-Hartmann and Hartmann screen wavefront aberrometers.

FIG. 1 is a schematic diagram of an example wavefront aberrometer capable of producing images that are indicative of ocular aberrations. In particular, FIG. 1 is a simplified schematic of a Talbot-Moiré wavefront aberrometer 100. The Talbot-Moiré wavefront aberrometer 100 includes a laser source 102 that emits a probe beam of light 103 towards a beam splitter 104. The beam splitter 104 redirects the probe beam 103 to a patient's eye 106. The probe beam 103 propagates through the eye and scatters from the retina. The scattering of the probe beam 103 at the retina acts as a diffuse source located at the retina. The scattered light from the retina propagates back through the eye and exits through the pupil. The wavefronts of the exiting light have been aberrated by the structures of the eye (e.g., the cornea), thus encoding information about the ocular aberrations in the wavefronts. The aberrated wavefronts pass through the beam splitter 104 to the relay lenses 108, 110. The relay lenses 108, 110 are designed, in some embodiments, to relay the entrance pupil of the eye to the first of two reticles 112, 114. The two reticles 112, 114 can be, for example, Ronchi grids. They can also be Hartmann screens having periodic arrays of circular apertures.

The passage of light through the first Ronchi grid 112 creates a fringe pattern that is changed by the aberrated wavefronts. The distance between the first and second Ronchi grids 112, 114 is a multiple of the Talbot distance so that a high contrast pattern from the first Ronchi grid 112 appears at the plane of the second Ronchi grid 114 (as predicted by Fresnel diffraction theory). The second Ronchi grid 114 is rotated, in the plane perpendicular to the optical axis of the instrument, relative to the first Ronchi grid 112 so that a Moiré pattern is created beyond the second Ronchi grid 114. A Talbot-Moiré wavefront aberrometer is described in more detail in U.S. Pat. No. 6,736,510, which issued on Feb. 4, 2003 and is entitled "OPHTHALMIC TALBOT-MOIRÉ WAVEFRONT SENSOR," the entirety of which is hereby incorporated by reference in this disclosure. It should be understood that the optical elements described in FIG. 1, as well as their particular layout, are only intended as one illustrative example; there are many variations as to the specific optical elements and layouts that can be used.

A camera 116 images the Moiré fringe pattern. The image of the Moiré fringe pattern can be provided to a processing module 118 (e.g., computer hardware and/or software). The image of the Moiré fringe pattern collected by the camera 116 can be processed using, for example, image processing techniques and calibration data to extract information regarding the ocular aberrations of the eye, including the types and amounts of aberrations exhibited by the eye. Such ocular aberrations can be quantified as, for example, the coefficients of Zernike polynomials. The image processing module can also be designed to analyze the Moiré fringe pattern image and to output an objective quality metric that represents the quality of the Moiré fringe pattern image collected by the camera 116. This objective quality metric can be used, for example, as an indicator of the reliability of the aberration measurements derived from the Moiré fringe pattern image. In some embodiments, the objective quality metric is gradated, for example, such that it can assume an intermediate level between two extremes. In some embodiments, the objective quality metric is a numerical score. In some embodiments, the numerical score is normalized to give a value in a particular range, for example, the range from 1 to 10. In some embodiments, a qualitative objective quality metric (e.g., "Good," "Marginal," "Bad," etc.) is provided by the processing module 118 in place of, or in addition to, the quantitative objective quality metric.

Wavefront aberrometers, including the Talbot-Moiré wavefront aberrometer 100 illustrated in FIG. 1, find use in a variety of applications. These include, but are not limited to, ophthalmic applications such as refractive surgeries. In some embodiments, the Talbot-Moiré wavefront aberrometer 100 is adapted for use in cataract surgeries. In such cases, the Talbot-Moiré wavefront aberrometer 100 may be integrated with a surgical microscope of the type used by surgeons for performing cataract surgeries. An example of this type of integrated instrument is described in U.S. patent application Ser. No. 11/110,653, which was filed on Apr. 20, 2005 and is entitled "INTEGRATED SURGICAL MICROSCOPE AND WAVEFRONT SENSOR," the entirety of which is hereby incorporated by reference in this disclosure.

During cataract surgeries, a Talbot-Moiré wavefront aberrometer 100, for example, can be used to perform intraoperative phakic, aphakic, and/or pseudophakic refractive measurements of a patient's eye. These refractive measurements can include, for example, the magnitude of spherical power, and the magnitude and orientation of cylindrical power of the patient's phakic, aphakic, and/or pseudophakic eye. These refractive power measurements can be useful, for example, in determining an appropriate intraocular lens (IOL) to use to replace the patient's natural crystalline lens during the cataract surgery. For example, intraoperative sphere and cylinder measurements of the patient's eye taken by the Talbot-Moiré wavefront aberrometer 100 can serve as inputs to a calculation for determining IOL power. If the intraoperative sphere and cylinder measurements are accurate, then the IOL power calculation can accurately determine the strength of the IOL that will leave a patient's vision substantially emmetropic after cataract surgery. However, if the refractive power measurements taken by the wavefront aberrometer are inaccurate, then the potential for an acceptable post-operative surgical outcome is reduced. As discussed herein, the accuracy of refractive power measurements made by a wavefront aberrometer, whether it be a Talbot-Moiré aberrometer or some other type, may be dependent upon the quality of image data collected by the aberrometer since the ocular aberration measurements are generally obtained based at least in part on the image data.

Figure 2:
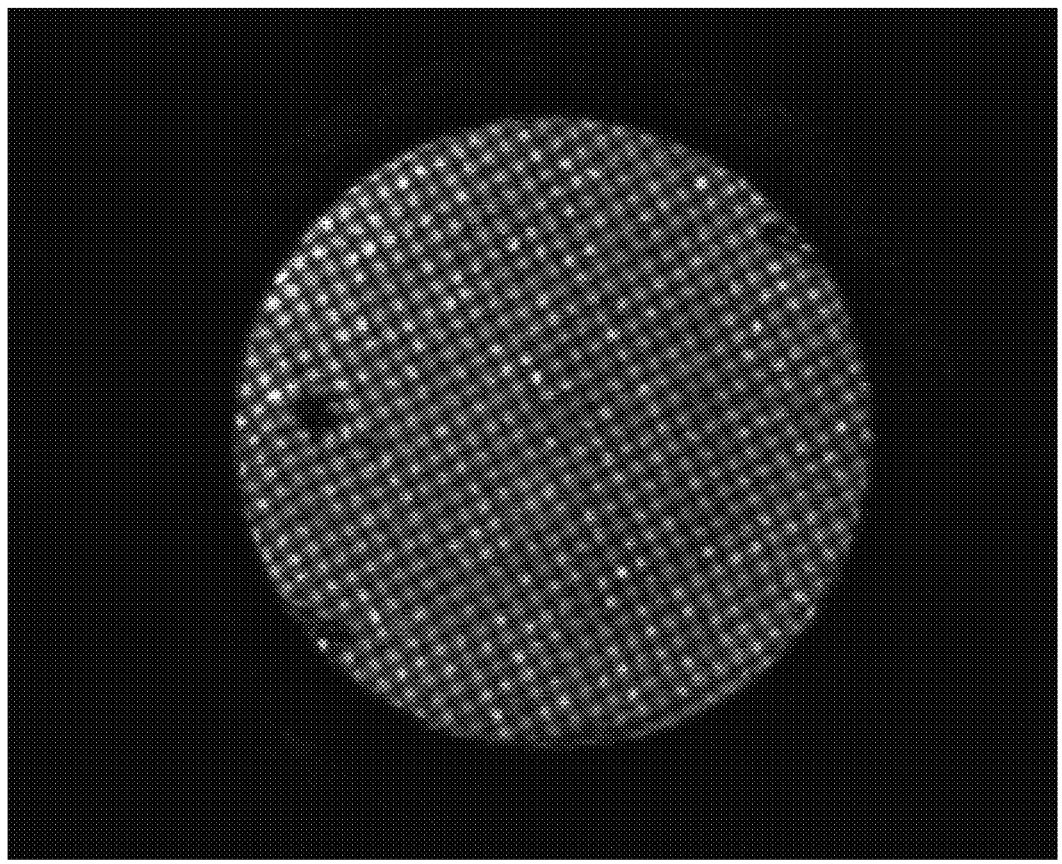
FIG. 2 is an example Moiré fringe pattern image 200 collected by a Talbot-Moiré wavefront aberrometer.

FIG. 2 is an example Moiré fringe pattern image 200 collected by a Talbot-Moiré wavefront aberrometer. The Moiré fringe pattern image 200 includes a generally round region with a pattern of spots and shadows appearing on a dark background. The generally round region is a result of the probe beam 103 that scatters from the retina and is apertured by the pupil as it exits the eye. The spots and shadows within the round region result from the passage of light between the grid lines of the first and second Ronchi grids 112, 114. During an examination of a patient's eye, typically multiple such Moiré fringe pattern images are collected (e.g., several tens of separate still images) over a period of time on the order of a second or some fraction of a second. Refractive power measurements such as spherical and cylindrical power can be obtained from an individual Moiré fringe pattern image 200 or collectively from more than one of the images.

The Moiré fringe pattern image 200, or a temporal series of images, can be preprocessed by, for example, the processing module 118 using a variety of techniques, including, but not limited to, spatial, temporal, or statistical filtering, transforming, contrast adjustments, averaging, denoising, thresholding, segmentation, feature detection and registration, etc. For example, in some embodiments, the plurality of images collected by the aberrometer can be analyzed to determine the ocular characteristics implied by each image (e.g., spherical and/or cylindrical power) and outlier images can be discarded (e.g., those images that imply a spherical power value greater than 1.5 standard deviations from the mean spherical power value can be discarded, etc.). After preprocessing, in some embodiments, each Moiré fringe pattern image 200 is Fourier transformed to the spatial frequency domain. Other types of transforms can also be used including, for example, wavelets, the cosine transform, and/or the Hartley transform.

The spatial frequency domain representation (e.g., the Fourier-transformed image) of a typical Moiré fringe pattern image 200 includes a central peak, which represents the DC component of the image, along with four main outer peaks arranged about the center peak, as known by those who practice the art. This general spatial frequency pattern follows from the simplified conceptual view of the Moiré fringe pattern as a first set of parallel stripes (e.g., formed by spots) and a second set of parallel stripes (e.g., formed by spots) that cross one another, the parallel stripes resulting from the Moiré interference pattern of light passing through the Ronchi grids 112, 114, or other diffractive optical elements (e.g., Hartmann screens), (each set of parallel stripes can be thought of as approximating a sinusoidal wave, whose Fourier transform is generally two peaks, the positions of which indicates the angular orientation of the sinusoidal wave). The spatial frequency of the sets of parallel stripes in the Moiré interference pattern depends upon, for example, the relative angle between the orientation of the first and second Ronchi grids, 112, 114. Two of the four main outer peaks represent redundant information which, in some embodiments, may be disregarded. The positions of the two remaining primary outer peaks are indicative of the spherical and cylindrical power of the patient's eye. For example, the two outer peaks rotate about the central peak, with a fixed relative spatial relationship between the two peaks, as the amount of spherical power changes because different amounts of spherical power result in the parallel stripes in the Moiré fringe pattern being rotated to different angular orientations. The relative spatial relationship between the two peaks changes as a result of changes in cylindrical power because changes in cylindrical power affect the angular orientation of the two sets of parallel stripes differently.

Determination of spherical and cylindrical power of the patient's eye from the Moiré fringe pattern image 200 generally involves determining and quantifying the locations of the primary outer peaks in the spatial frequency domain. The locations of these peaks can be more accurately and precisely determined when the transformed spatial frequency image data exhibits certain characteristics described more fully herein (e.g., the spatial frequency peaks are sharp and well-defined). Similarly, accurate and precise ocular aberration measurements are more likely to be obtained from a spatial-domain Moiré fringe pattern image 200 that exhibits certain characteristics described more fully herein. In some embodiments, the technique for determining an objective quality metric for a given set of wavefront aberrometer image data includes the application of one or more functions/operations to determine the extent to which the wavefront aberrometer image data, both in the spatial and spatial frequency domains, exhibits the certain characteristics that are generally indicative of high-quality aberrometer image data. The characteristics that are found to be indicative of high-quality aberrometer image data may vary depending upon the type of wavefront aberrometer image data being analyzed. However, the techniques described herein for calculating an objective quality metric can be adapted for the image data from other types of wavefront aberrometers.

In some embodiments, a calculation of a quantitative objective exam quality metric, Q, for a particular set of wavefront aberrometer image data is generally represented by Equation 1.

$$Q = \sum_{n=1}^{N} C_n F_n(Y) \qquad (1)$$

In some embodiments, Y represents an input wavefront aberrometer image (e.g., the spatial-domain Moiré fringe pattern image 200 and/or the spatial frequency-domain representation of the image 200). In some embodiments, $F_n(Y)$ represents a set of N functions (e.g., scalar functions) of the input image Y. Each of $F_n(Y)$ may be a function of a single wavefront aberrometer image or of a series of M such aberrometer images. In addition, each of $F_n(Y)$ may involve, for example, a single mathematical operation or multiple mathematical operations. In some embodiments, each of $F_n(Y)$ outputs a scalar value. However, the output may also be, for example, a vector, a matrix, etc. In some embodiments, the resulting output from each of the N functions $F_n(Y)$ is weighted by a corresponding coefficient $C_n$. In some embodiments, each weighting coefficient is a scalar value. However, the weighting coefficients can also be, for example, vectors, matrices, etc. In some embodiments, the summation in Equation 1 can also include cross terms such as, for example, $C_k F_1(Y) F_2(Y)$, or other higher-order terms, etc.

In some embodiments, the sum of the weighted outputs of the functions $F_n(Y)$ is added to a constant value $C_0$, as in Equation 2.

$$Q = C_0 + \sum_{n=1}^{N} C_n F_n(Y) \qquad (2)$$

In some embodiments, the weighted sum of outputs of the functions $F_n(Y)$ is subjected to a normalization and/or thresholding operation to keep the final value of the image quality Q in a desired range (e.g., 1 to 10). In some embodiments the lower end point of the normalized range represents the highest possible exam quality, while the upper endpoint represents the lowest possible exam quality. Of course, the reverse meaning could also be applied. In some embodiments, the normalization operation is linear such that equal steps in the value of the quantitative objective exam quality metric are representative of equal steps in the value of the weighted sum of outputs of the functions $F_n(Y)$. In other embodiments, however, the normalization operation could be set on a logarithmic scale, or some other desired scale.

As discussed herein, the objective quality metric may be based on a sum (weighted or otherwise), or some other aggregate (e.g., Boolean combination, fuzzy logic combination, etc.), of a plurality of image characteristics. This is advantageous because a particular wavefront aberrometer image may be of relatively poor quality as judged by one particular characteristic, while the same image may be of relatively high quality as judged by another characteristic. The image characteristics can affect the objective quality metric in an interdependent fashion rather than an independent fashion (e.g., in some embodiments, no single poor image characteristic will disqualify a particular wavefront aberrometer image if it is counterbalanced by a different exceptional image characteristic). Since the objective quality metric is based on an aggregate of multiple characteristics, a better representation of the overall image quality is obtained. It may be that the good aspects of the image outweigh the bad, or vice versa. If the good characteristics of the image outweigh the bad, the situation where an image is discarded based on one poor characteristic, or a poor subset of the considered characteristics, can be avoided. This can result in less loss of usable image data by disqualification for poor image quality. By the same token, if the bad characteristics outweigh the good, the image can be discarded even though it may appear to be of good quality based on one good characteristic, or a good subset of the considered characteristics.

For example, an image may be scored as a "1" (high quality) for a first characteristic and a "7" (relatively low quality) for a second characteristic, resulting in a total averaged score of "4" (relatively high quality). In such a case, a threshold for use/non-use of an image may have been set at "5" such that the image would be used in the calculation of ocular aberration measurements. If, instead, the objective quality metric had been based on each image characteristic separately, then it may have been disqualified based on the "7" assigned for the second characteristic. In other words, a relatively high quality image may have been discarded were it not for the fact that the objective quality metric was based on an aggregate of multiple image characteristics. This example also illustrates the advantages of gradated objective quality metrics. An image can be scored with intermediate values rather than being identified simply as "good" or "bad." Gradated objective quality metrics give greater capability for comparing one image with another even in situations where a number of different image characteristics can affect overall image quality in complex ways. In some embodiments, the interdependence of the objective quality metric on the image characteristics is advantageous because it can reduce the amount of acceptable image data that may otherwise be discarded, potentially increasing the speed of the exam procedure since it may reduce whatever need may exist to collect additional image data in light of such discarded images.

For a given set of functions $F_n(Y)$, the values of the weighting coefficients $C_n$ can be selected based on a training set of image data according to, for example, an optimization process. For example, the weighting coefficients $C_n$ can be set so as to reduce or minimize, in some sense (e.g., in the least-squares sense), the collective error between the values of the objective quality metric calculated for a series of test wavefront aberrometer images and subjective quality metric values assigned to the same series of test images by a human expert.

Given a set of functions, test image data, and subjective expert scores of the test image data, an optimization process can be used to select the coefficients $C_n$ for n=0, 1, . . . N, so that the calculated values of the objective exam quality metric Q collectively correlate to the corresponding subjective values assigned by the human expert. Owing to the multi-modal and non-linear nature of Equations (1) and (2), a global optimization method such as a simulated annealing method is well-suited for determination of the weighting coefficients $C_n$. Simulated annealing is an optimization algorithm known to those who practice the art. Other optimization processes can also be used such as, for example, an exhaustive search, multiresolution exhaustive search, genetic algorithms, least-squares fitting, etc. The processes employed need not yield the most optimal solution but rather a solution that gives an acceptable level of accuracy in the calculation of objective quality metrics.

Figure 3:
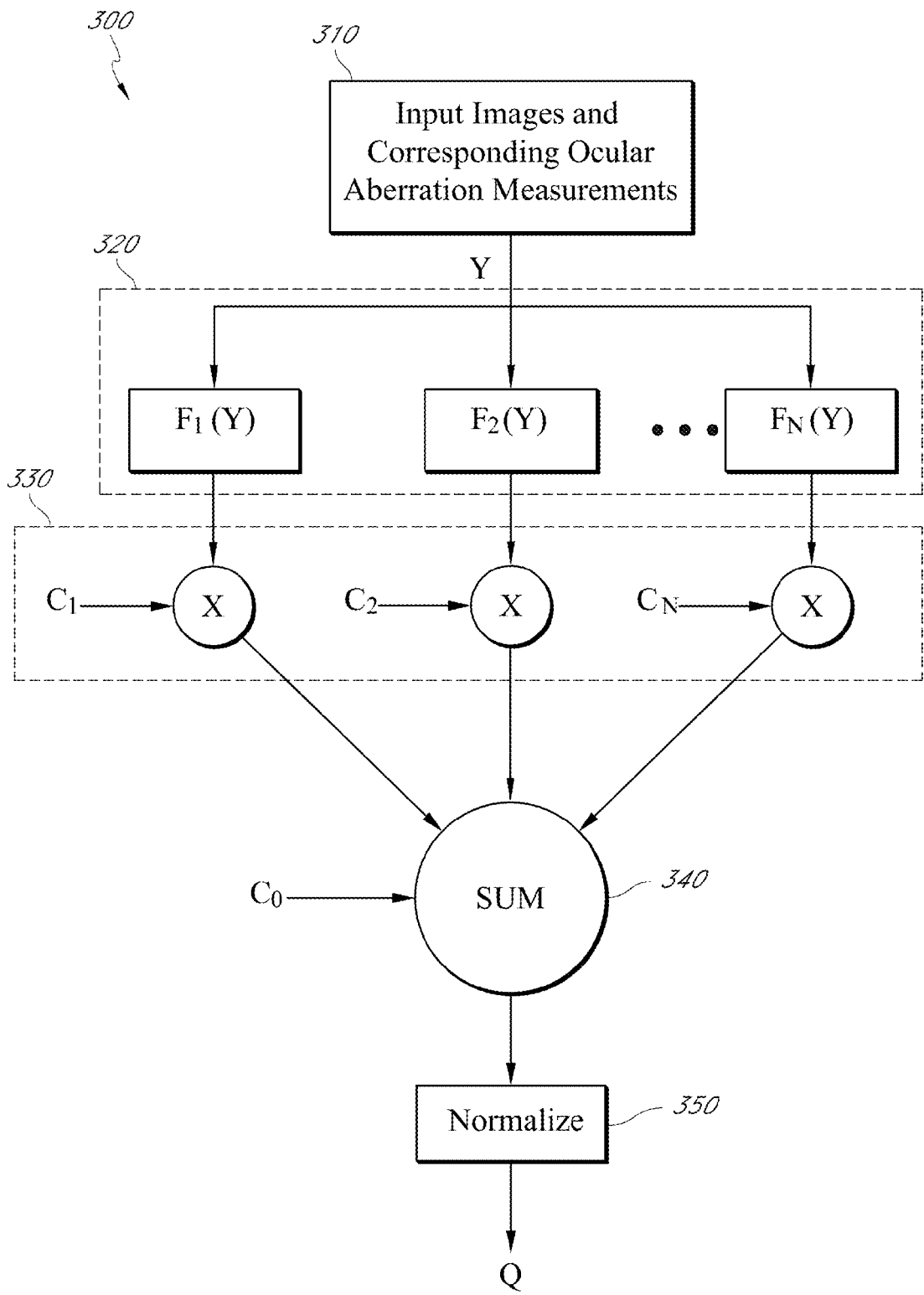
FIG. 3 is an overview flow chart of a method for calculating an objective quality metric for wavefront aberrometer image data.

FIG. 3 is an overview flow chart of a method 300 for calculating an objective quality metric, Q, for wavefront aberrometer image data. FIG. 3 shows a diagram of the calculation indicated in Equation (2). The method 300 begins at block 310 with inputting a sequence of M captured Moiré fringe pattern images (e.g., 200). The corresponding ocular aberration measurements, or other data, obtained from the M images can also be optionally inputted. At block 320, the outputs of a set of N (N being the number of scalar functions) scalar valued functions $F_n(Y)$ are calculated. The output of each scalar function $F_n$ is multiplied by a corresponding scalar coefficient $C_n$ at block 330. The sum of the coefficient-weighted output of the functions $F_n(Y)$, plus an additional constant $C_0$, is then formed at block 340. Finally, the resultant value is normalized at block 350 and the objective quality metric Q is then outputted. It should be understood that not all of the blocks included in the method 300 are required, and that they can be adapted or reorganized in different ways to suit different calculations of the objective quality metric Q.

In some embodiments, the objective quality metric is outputted to a user. If the quality metric indicates relatively poor quality aberrometer image data, then the user may be granted the option of obtaining additional or new image data. In contrast, if the quality metric indicates relatively good quality image data, then the user may instead choose to continue with the ocular aberration measurements obtained from the set of image data inputted at block 310. Alternatively, the processing module 118 could be programmed with a threshold quality metric value such that any image data with a quality metric poorer than the threshold can be automatically disregarded and new image data obtained. This process can be performed iteratively until image data with an adequate objective quality metric is obtained. Other uses of the objective quality metric are also possible.

Figure 4:
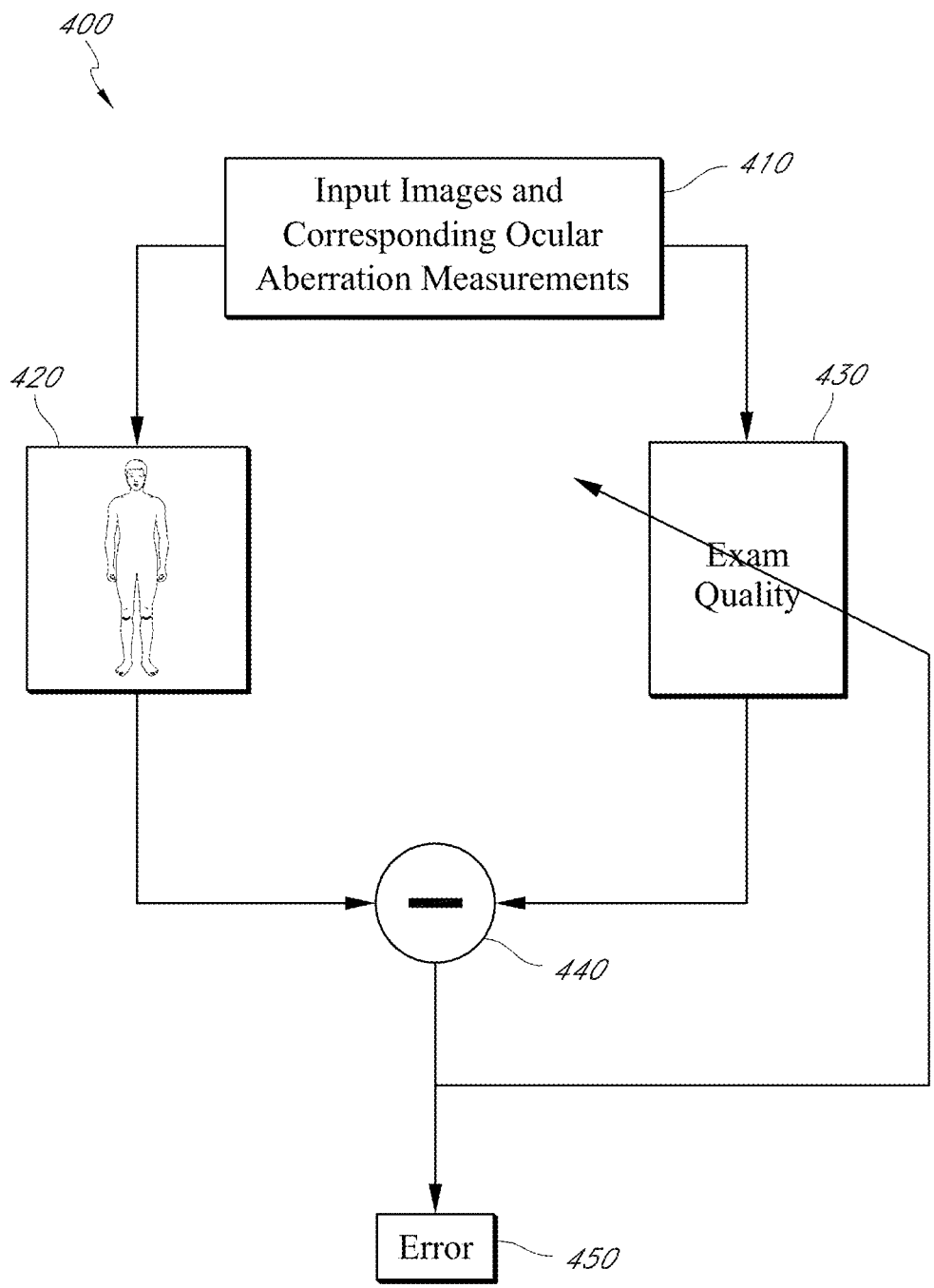
FIG. 4 is an overview flowchart of a method for determining one or more parameters for use in calculating an objective quality metric for wavefront aberrometer image data using a set of training images and a human expert.

FIG. 4 is an overview flowchart of a method 400 for determining one or more parameters (e.g., the weighting coefficients $C_n$) for use in calculating an objective quality metric for wavefront aberrometer image data using a set of training images and a human expert. The method 400 begins at block 410 where a training set of wavefront aberrometer image data (e.g., multiple Moiré fringe pattern images 200 collected from multiple eyes) is provided, optionally along with the corresponding ocular aberration measurements obtained from the data.

In some embodiments, the training set of image data is carefully selected to have characteristics that are representative of a satisfactory range of wavefront aberrometer images that are collected under normal examination conditions. For example, the training set of image data may include wavefront aberrometer images collected from a variety of eyes exhibiting a variety of ocular aberrations. In addition, the training set of image data may include a variety of image features commonly encountered during normal examination conditions. For example, in the case of Talbot-Moiré wavefront aberrometer images, the training set of image data may include images where the circular region which includes the fringe pattern is centered and others where it is decentered; some where the image contrast is good and others where it is poor; some where air bubbles are present and others where they are absent; some where the fringe patterns are distorted and others where they are regular; and some where the spatial frequency peaks are well-defined and others where they are not, etc.

At block 420, the test set of image data is examined by a human expert who assigns one or more subjective quality metrics to the data. For example, the human expert may assign a subjective quality score to each of the individual wavefront aberrometer images. In some embodiments, this is a numerical score in the range from, for example, 1-10. At block 430, the processing module 118 calculates one or more objective quality metrics for the same test set of image data. For example, the processing module 118 may calculate an objective quality score for each of the wavefront aberrometer images provided using, for example, the methods described herein. Again, in some embodiments, the objective quality metric is a score in the range from, for example, 1-10.

The calculation of the objective quality metric may involve an implementation of, for example, Equation (1) or (2). An initial, or non-final, set of weighting coefficients $C_n$ can be used in the calculation until such time as appropriate values for the coefficients $C_n$ are determined. At block 440, the error between the subjective quality metrics assigned by the human expert and the objective quality metrics calculated by the processing module 118 is found. The error data can then be outputted, at block 450, to an optimization module and used to iteratively update or refine the calculation of the objective quality metrics at block 430 in a manner so as to reduce the error calculated at block 440.

In some embodiments, the refinement of the objective quality metric calculation involves adjusting the weighting coefficients $C_n$ that are used in, for example, Equations (1) and (2) so as to reduce the error calculated at block 440. Based upon the difference between the human expert subjective scores and the exam quality objective scores, the coefficients $C_n$ for n=0, 1, ... N, can be modified until the error is reduced or is as small as possible, as small as practicable, or as small as desired, for example. In some embodiments, the optimization module uses a simulated annealing technique. In some embodiments, this coefficient optimization procedure is only implemented initially; the processing module 118 can be programmed with the resulting coefficients $C_n$ and used to calculate objective quality metrics for wavefront aberrometer image data that does not belong to the training set. In some embodiments, the coefficients $C_n$ are limited to a particular range of values during the optimization process for calculating the coefficients. For example, some of the coefficients may be restricted to a particular range that has physical meaning given the corresponding function $F_n$. In some embodiments, some of the coefficients are restricted to have positive values since negative values may not be logical.

In some embodiments, the coefficients $C_n$ could be determined so as to reduce or minimize the error between the objective quality metrics calculated, as in Equations (1) and (2), and objective quality metrics calculated using a different method or using a different set of training data. In addition, the coefficients $C_n$ could be determined so as to reduce or minimize the error as compared to an analytically derived set of scores. For example, such a set of scores could be analytically derived based, at least in part, on a principal components analysis to determine the relative amounts of variation in image quality explained by each of multiple functions $F_n(Y)$.

It should be appreciated that other methods of calculating objective quality metrics for wavefront aberrometer image data are also available. These include, for example, neural networks, fuzzy logic or clustering, or combinations thereof. These techniques may similarly involve the determination of calculation parameters (e.g., neural network node weights) that, once found, allow a computer or other processing device to perform a complex task, such as differentiating high-quality wavefront aberrometer image data from low-quality image data. The usage of these techniques and the determination of the necessary calculation parameters are known to those who practice the art.

Figure 5:
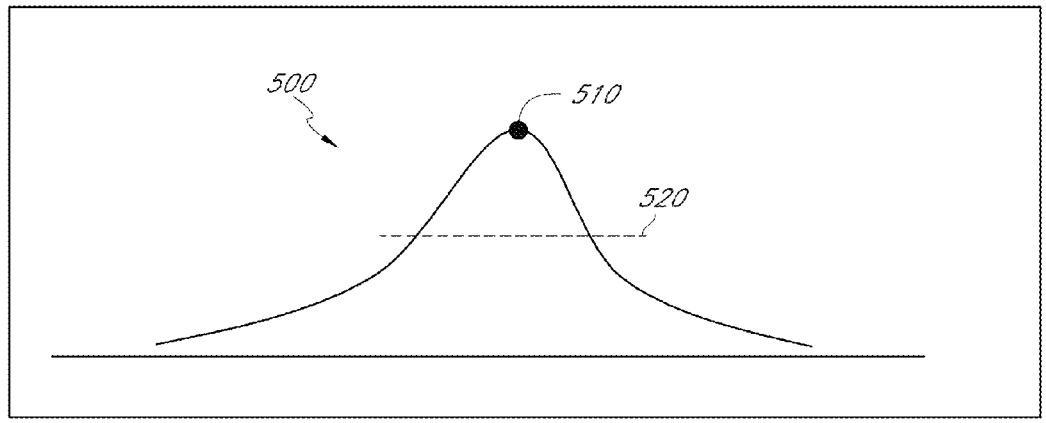
FIG. 5 illustrates an example cross-sectional profile of a spectral peak in a frequency domain representation of wavefront aberrometer image data.
Figure 6:
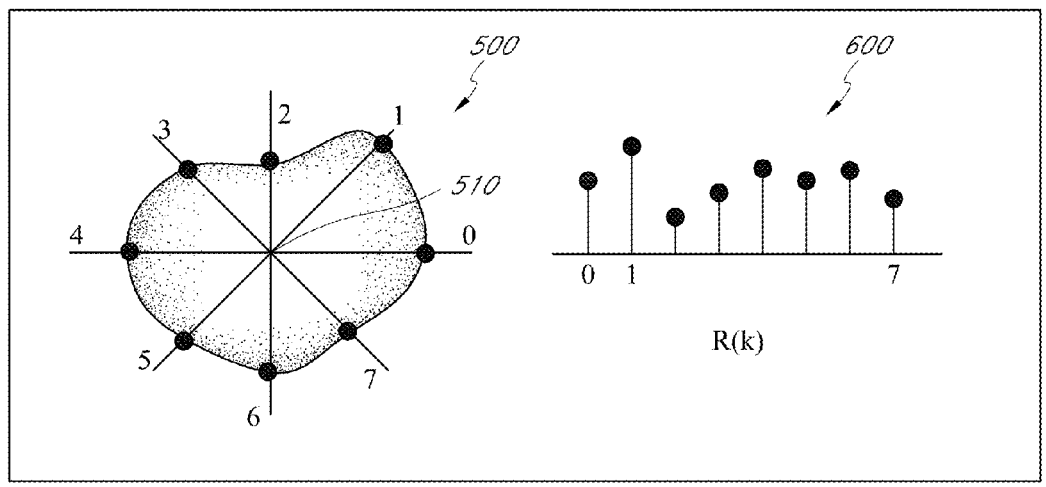
FIG. 6 illustrates an example contour of the spectral peak of FIG. 5, and a plot showing the distance from the center of the peak to its edge in eight directions.
Figure 7:
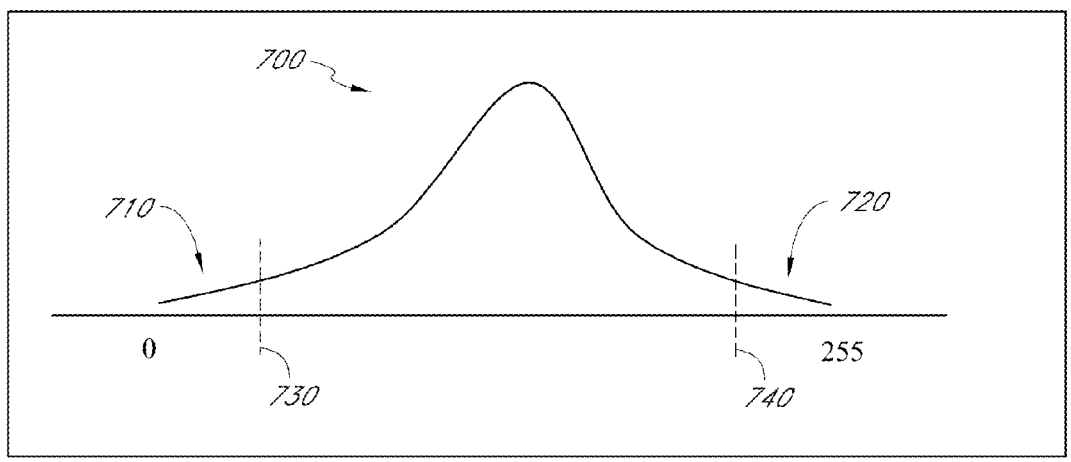
FIG. 7 illustrates an example histogram of pixel intensity values in wavefront aberrometer image data, the histogram being indicative of image contrast.

FIGS. 5-7 illustrate example functions $F_n(Y)$ that can be used, for example, according to Equations (1) and (2) to calculate objective quality metrics for wavefront aberrometer image data. Nine such functions are described herein, though many others are possible and can be used in various embodiments. In some embodiments, $F_1(Y)$ is a function whose output relates to the centration of all or a portion of a captured wavefront aberrometer image. For example, $F_1(Y)$ may quantify the degree to which an image is centered within the wavefront aberrometer camera frame (e.g., camera 116). With respect to the Talbot-Moiré wavefront aberrometer 100, in some embodiments, $F_1(Y)$ quantifies the extent to which the circular region containing the Moiré fringe pattern is centered within the camera 116 frame.

In some embodiments, the Talbot-Moiré wavefront aberrometer 100 obtains more accurate refractive power measurements when it is aligned with respect to the patient's eye such that the circular region outlining the Moiré fringe pattern is centered in the camera 116 frame. Thus, $F_1(Y)$ quantifies the centration of this region. If this circular region is decentered with respect to the center of the image frame, some misalignment of the subject may have occurred which can lead to a degradation in the quality of the resulting refractive power measurements. In other embodiments, $F_1(Y)$ may instead quantify the extent to which the circular region containing the Moiré fringe pattern is shifted from some other point within the frame other than the center.

In some embodiments, the output of $F_1(Y)$ quantifies the distance in, for example, pixels of the camera's 116 image sensor array, from the center of the image frame to the center (e.g., the centroid) of the circular region in the Moiré fringe pattern image 200. In other embodiments, the output of $F_1(Y)$ can quantify the displacement (e.g., in pixels) between any identifiable feature in the aberrometer image and the center, or any other predetermined location, in the image frame. The feature of interest in the wavefront aberrometer image can be identified using image processing feature detection techniques known to those who practice the art. In the case of a series of M multiple Moiré fringe pattern images (e.g., 200) obtained during an ocular examination, $F_1(Y)$ can output a vector with a centration value for each of the multiple images or a single value representative of the overall degree of centration for the M images. In some embodiments, the single representative value is an arithmetic mean centration value for the M images. In other embodiments, it may be a geometric mean value, a median value, etc.

While image quality of wavefront aberrometer image data is an indicator of exam quality, the consistency of ocular aberration measurements obtained from a series of M images can also be an indicator of exam quality. For example, if each of a series of M images collected during an ocular examination each yields ocular aberration measurements (e.g., spherical and cylindrical power) that are similar to one another, in some embodiments this may be taken as an indication that the exam quality for the M images was relatively good since they yielded repeatable ocular aberration measurements. Thus, some of the functions $F_n(Y)$ may be used to quantify the consistency of ocular aberration measurements obtained from a series of wavefront aberrometer images collected during an ocular examination.

In some embodiments, the output of $F_2(Y)$ quantifies the consistency of one or more ocular aberration measurements obtained from a set of wavefront aberrometer image data. Each of a series of M wavefront aberrometer images can typically yield, for example, a spherical power value, a cylindrical power value, and a cylindrical axis value. These sphere, cylinder, and axis values can be calculated by the processing module 118 using methods known to those skilled in the art. In some embodiments, $F_2(Y)$ may quantify the consistency of spherical or cylindrical power values calculated from each of a series of M wavefront aberrometer images. In other embodiments, the consistency of other ocular aberration measurements may be quantified in place of, or in addition to the spherical and cylindrical power values. The consistency of an ocular aberration value over a series of M wavefront aberrometer images collected during an ocular examination can be quantified by, for example, a measure of the variance or standard deviation of the set of ocular aberration values calculated from the M images.

In some embodiments, the output of $F_2(Y)$ is the standard deviation of the spherical equivalent refractive power calculated from a series of M wavefront aberrometer images. The spherical equivalent $SEQ_m$ of the mth measurement is calculated as in Equation (3).

$$SEQ_m = Sphere_m + \frac{Cylinder_m}{2} \quad (3)$$

That is, the SEQ for the mth image is equal to the sphere value from the mth image plus half of the cylinder value from the mth image. The units for SEQ can be given in diopters. The arithmetic mean (MEAN) and standard deviation (SD) of the SEQ values are calculated as in Equations (4) and (5), respectively, where the SEQ values take the place of the X variable in the calculation of the $F_2(Y)$ output.

$$MEAN = \frac{1}{M} \sum_{m=0}^{M-1} X_m \quad (4)$$

$$SD = \sqrt{\frac{1}{M} \sum_{m=0}^{M-1} [X_m - MEAN]^2} \quad (5)$$

Similarly, in some embodiments, the output of $F_3(Y)$ is the standard deviation of the cylinder value from each of a series of M wavefront aberrometer images. As described above, the cylinder values can be computed for each acquired image using methods known to those skilled in the art. The output of $F_3(Y)$ is calculated using equations (4) and (5) where the cylinder values take the place of the X variable.

Some of the $F_n(Y)$ functions operate on a spatial frequency representation (e.g., the spatial Fourier transform) of wavefront aberrometer image data. As discussed herein, in the processing of the Talbot-Moiré wavefront aberrometer images, a Fourier transform may be performed so as to analyze and identify characteristics of spectral peaks in the data. The exact location of, for example, two primary spectral peaks can be used, for example, to determine the sphere, cylinder, and axis of the sphero-cylindrical correction to best correct the eye's ocular aberrations. The size and definition of spatial frequency peaks in the transformed image data can be indicative of the quality of the collected image data. If these peaks are very well formed and sharp, the sphere, cylinder, and axis measurements can often be determined with more accuracy and precision.

In some embodiments, the outputs of $F_4(Y)$ and $F_5(Y)$ are indicative of size, definition, and/or shape of spectral peaks in transformed wavefront aberrometer data. In particular, $F_4(Y)$ and $F_5(Y)$ can measure the width of first and second spectral peaks in the transformed image data, whether in the direction of a single axis or in the directions of multiple axes. In some embodiments, the outputs of $F_4(Y)$ and $F_5(Y)$ are the mean spectral peak width of, for example, two respective primary peaks in the Fourier transform of acquired Talbot-Moiré wavefront aberrometer image data. In some embodiments, $F_4(Y)$ and $F_5(Y)$ measure the width of respective spectral peaks in multiple directions from the respective centers of the peaks. In some embodiments, these functions output either the peak widths in each of the multiple directions, or single values representative of the widths in the multiple directions (e.g., a mean width). In other embodiments, one or more of $F_n(Y)$ may be indicative of characteristics of spatial-domain peaks in wavefront aberrometer image data rather than spectral-domain peaks.

FIG. 5 illustrates an example vertical cross-sectional profile of a spectral peak 500 (where, for example, the brightness of image pixels has been plotted as a two-dimensional function of position on the image) in a spatial frequency-domain representation of wavefront aberrometer image data. The cross-sectional profile can be taken through any selected meridian of the peak 500. In some embodiments, the processing module 118 identifies the center location 510 of the spectral peak 500. There are various definitions that can be used to define the center location 510. For example, the center location 510 could mark the maximum value in the neighborhood of the spectral peak 500, the midpoint between the identified edges of the spectral peak 500, the location of the centroid of the peak 500, etc. The processing module 118 can also quantify the width 520 of the spectral peak 500. This width measurement may be a full width at half maximum (FWHM) measurement or some other indicator of peak width.

The width of the peak 500 can be found by searching pixels to the right of the center location 510 until finding a value that is, for example, one half the value at the center location 510. This can be taken as the right boundary. A similar operation can be performed to identify the left boundary. The width of the peak 500 can then be defined as the distance between the left and right boundaries, though, of course, many other different definitions of the width of the peak can also be used. The width of the spectral peak 500 may be calculated in a single direction, as shown in the cross-sectional view presented in FIG. 5. In some embodiments, however, the width of the spectral peak 500 is calculated in multiple directions from, for example, the center point 510 of the peak 500, as illustrated in FIG. 6.

FIG. 6 illustrates an example contour (e.g., from a top view) of the spectral peak 500 of FIG. 5, and a plot 600 showing the distance from the center 510 of the peak 500 to its edge in eight directions. The cross-sectional profile of the peak 500 represents, for example, a horizontal slice through the peak at a selected height (e.g., half of the maximum height). The center 510 of the peak 500 is indicated at the intersection of four crossing lines. The width of the peak 500 can be calculated in each of the directions indicated in FIG. 6 (i.e., the line connecting 0 and 4, the line connecting 1 and 5, the line connecting 2 and 6, and the line connecting 3 and 7). These multiple widths can be calculated as described above. The width values can be denoted, for example, as total width of the peak in a given direction (e.g., the distance from point 0 to point 4) or as the "radius" of the contour in a selected direction. For example, the "radius" of the contour can be defined, in some embodiments, as the distance from the center point 510 to the boundary of the contour in a selected direction (e.g., the distance from the center point to point 0 or the distance from the center point to point 4) and for a selected height. The width of the peak 500 can be calculated in any number of directions, whether equally angularly spaced or not.

The widths of the peak 500 in the multiple directions can be stored, for example, in an array denoted R(k). FIG. 6 shows an example plot of the "radius" values R(k) of the peak 500. In some embodiments, the output of $F_4(Y)$ is the array of "radius" values R(k) for a selected peak or the arithmetic mean of the R(k) "radius" values. In other embodiments, the output of $F_4(Y)$ can be some other value or values indicative of the width of a peak in one or more directions. In some embodiments, $F_4(Y)$ measures the width of one of the two primary spectral peaks in a Fourier-transformed Moiré fringe pattern image (e.g., 200). In some embodiments, the output of $F_5(Y)$ similarly quantifies the width of the second of the two primary spectral peaks. For the case where the wavefront aberrometer image data includes a sequence of M separate images captured during an ocular examination, the outputs of $F_4(Y)$ and $F_5(Y)$ can be, for example, the mean of the width value or values calculated for each individual image.

In some embodiments, $F_6(Y)$ quantifies the regularity (e.g., roundness) of a spatial-domain peak or frequency-domain peak (e.g., the first of the two primary spectral peaks in the Fourier transform of an acquired Moiré fringe pattern image) in wavefront aberrometer image data. For example, $F_6(Y)$ can quantify the range of the widths of a frequency-domain peak 500 in multiple directions as a measure of the regularity of the shape of the peak 500. In some embodiments, $F_6(Y)$ can use the distance array R(k) from the calculation of $F_4(Y)$ and $F_5(Y)$. The range of widths around the peak 500 can be calculated as the maximum value in the R(k) array (i.e., the maximum "radius" of the peak 500) minus the minimum value in the R(k) array (i.e., the minimum "radius" of the peak 500). This is illustrated in Equation (6) for $F_6(Y)$.

$$F_6(Y) = \max[R(k)] - \min[R(k)] \quad (6)$$

It should be understood, however, that many other measures of the regularity of a peak in wavefront aberrometer image data can also be used. In some embodiments, $F_7(Y)$ similarly quantifies the regularity or irregularity of a second peak in the image data (e.g., the second of the two primary spectral peaks in the Fourier transform of an acquired Moiré fringe pattern image). For the case where the wavefront aberrometer image data includes a sequence of M separate images captured during a patient examination, the outputs of $F_6(Y)$ and $F_7(Y)$ can be the mean, or some other representative value, of the peak regularity value or values calculated for each individual image.

In some embodiments, $F_8(Y)$ measures image contrast in wavefront aberrometer image data. For example, image contrast can be quantified based on a histogram of all, or a portion of, the brightness values in the image data. In particular, the histogram spread can be used as a measure of image contrast. Generally, higher contrast images can lead to more accurate and precise ocular aberration measurements from the wavefront aberrometer image data. FIG. 7 illustrates an example histogram 700 that shows the number of pixels with a given brightness value plotted as a function of pixel brightness. In the case of 8-bit image data, the brightness values run from 0 to 255, though the number of distinct brightness values can vary depending upon hardware and software implementation of the wavefront aberrometer. There are other methods of quantifying image contrast that can also be used in various embodiments.

The histogram 700 may be calculated for an entire wavefront aberrometer image, or for only a subset of the image (e.g., an identified feature or region of interest). In the case of a Moiré fringe pattern image (e.g., 200) collected from a Talbot-Moiré wavefront aberrometer, in some embodiments, the histogram 700 is calculated only for image pixels that lie within the circular boundary that encloses the fringe pattern. In other embodiments (e.g., where image data from different types of wavefront aberrometers is being analyzed), contrast can be determined for different features or regions of interest within the image.

In some embodiments, the processing module 118 begins by applying known image processing algorithms to identify specific features or regions of interest, if any, from which to calculate one or more histograms. The processing module 118 may then calculate one or more histograms from the identified image data. In some embodiments, the processing module 118 calculates the histogram for the region of one or more Moiré fringe pattern images (e.g., 200). FIG. 7 is an example of the resulting histogram. In some Embodiments, once the histogram has been calculated, the processing module 118 identifies upper and lower endpoints from which to calculate histogram spread (greater spread being indicative, for example, of greater image contrast). For example, the lower end point 730 may be taken as the point at which only 10% of the pixels 710 have a lower brightness value. Similarly, the upper end point 740 may be taken as the point at which only 10% of the pixels 720 have a higher brightness value. In other embodiments, different end points can be used. In some embodiments, the output of $F_8(Y)$ is computed as in Equation (7), where $X_{90}$ is the upper end point 740 while $X_{10}$ is the lower end point 730.

$$F_8(Y) = X_{90} - X_{10} \quad (7)$$

In the case where the wavefront aberrometer image data being analyzed includes a sequence of M images, for example from a single ocular examination, the output of $F_8(Y)$ can be, for example, the arithmetic mean of the histogram spread calculated from like features or regions of interest in each individual image.

In some embodiments, $F_9(Y)$ measures image contrast in yet another way. For example, $F_9(Y)$ can be used to quantify histogram spread, or some other measure of image contrast, in a way such that the effect of glint (caused by light reflecting off the cornea) or other localized image defects on the calculation is reduced. Glint can result in a relatively large region of bright pixels which can tend to mask the underlying ocular aberration information. The effect of localized defects in the image data on the contrast calculation can be reduced, for example, by calculating multiple localized contrast values and then selecting one such localized contrast value that is generally representative of the contrast of a larger portion of the image (e.g., the image as a whole). For example, the processing module 118 can calculate histograms in multiple sub-regions that are non-overlapping or that do not fully overlap. In some embodiments, these are 64×64, or 20×20 non-overlapping square regions of pixels in the area of a Moiré fringe pattern image (e.g., 200), though other sizes and shapes of sub-regions can also be used.

The number of pixels in each of these sub-regions may not necessarily be equal to 2048 since some of the square sub-regions may intersect the edge of the circular boundary surrounding the fringe pattern. In some embodiments, the processing module 118 sums the number of pixels in each sub-region and discards those sub-regions that do not contain a full 2048 pixels, though, this is not required. The processing module 118 then identifies a representative sub-region (a sub-region whose contrast is adequately representative of the remainder of the image) from which to calculate, for example, the histogram spread.

A representative sub-region can be identified, for example, by calculating the mean brightness value for each sub-region using its histogram, then sorting the sub-regions based upon their mean brightness values, and selecting the median sub-region (half of the sub-region histograms having a mean value higher than the mean value of the median sub-region, and half having a mean value lower than the mean value of the median sub-region). The histogram of the median sub-region can then be used to calculate histogram spread, which can be used as the output of $F_9(Y)$. There are many other methods of identifying a representative sub-region with a histogram that is adequately representative of the contrast of the image.

Other functions $F_n(Y)$ can also be used in various embodiments. These include, for example, functions that represent wavefront aberrometer image data in terms of a Zernike polynomial expansion. Other image characteristics of the wavefront aberrometer image data could also be calculated and used in, for example Equations (1) and (2).

In some embodiments, the image characteristics, functions, and techniques described herein for determining an objective quality metric can be applied to image data from, for example, Moiré-Hartmann aberrometers and Shack-Hartmann aberrometers. For example, in the case of Shack-Hartmann aberrometers, similar techniques as are used for determining frequency-domain peak width and irregularity could be used to analyze spatial-domain peak width and domain of the spots created by a Shack-Hartmann aberrometer. Other image characteristics, functions, and techniques, as described herein, can also be applied.

In some embodiments, an objective quality metric is calculated for each of M images in a set of wavefront aberrometer image data (e.g., M separate images collected during a single ocular examination). In other embodiments, a single objective quality metric is calculated for all of the M images. In either case, once one or more objective quality metrics have been determined for a set of wavefront aberrometer image data, the metric or metrics can be used to determine whether the collected wavefront aberrometer image data is of adequate quality and whether additional wavefront aberrometer image data should be collected. This can be done automatically by the processing module 118, or with user input. In the case where the image data includes multiple images, objective quality metrics for each image can be used to determine which, if any, of the images will be used in the determination of ocular aberration measurements. For example, if each of the M wavefront aberrometer images in a set of image data is given an objective quality metric, then the image with the highest quality metric could be selected from which to determine the ocular aberration measurements. In some embodiments, the ocular aberration measurements calculated from each of a certain top percentage of images, as judged by their objective quality metrics, can be averaged together and output as the ocular aberration measurements.

FIGS. 8-12 are examples of Moiré fringe pattern images collected by a Talbot-Moiré wavefront aberrometer. Some of the Moiré fringe pattern images illustrated in FIGS. 8-12 are relatively high-quality images, while others are relatively low-quality images. Certain ones of the example images include image defects which can be successfully automatically detected using the equipment and techniques described herein.

Figure 8:
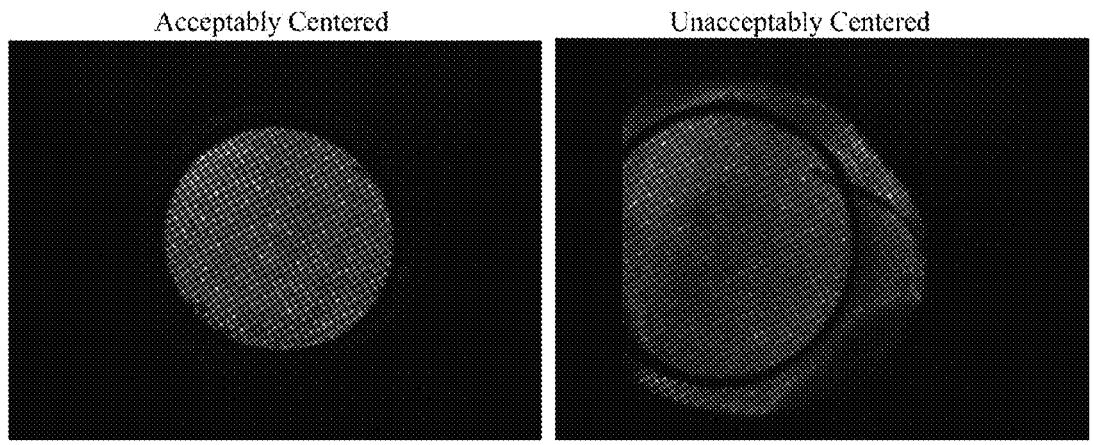
FIG. 8 illustrates two wavefront aberrometer images with different centration characteristics.

FIG. 8 illustrates two wavefront aberrometer images with different centration characteristics. The left hand image in FIG. 8 illustrates a Moiré fringe pattern where the circular region is acceptably centered in the image frame. The right hand image of FIG. 8, however, is an example of a Moiré fringe pattern image that is not acceptably centered in the frame. In some embodiments, a centration characteristic of wavefront aberrometer image data is quantified and accounted for in the objective quality metric calculation, for example, as described herein.

Figure 9:
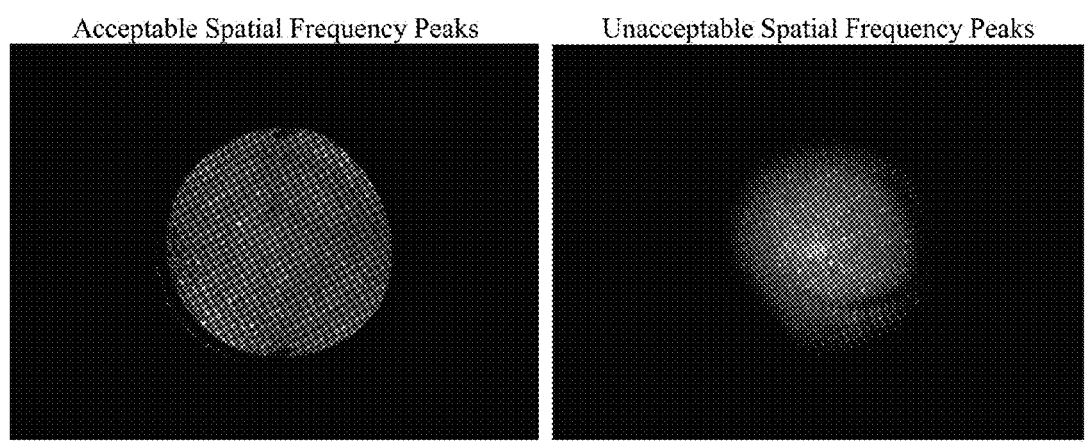
FIG. 9 illustrates two wavefront aberrometer images with different spatial frequency peak characteristics.

FIG. 9 illustrates two wavefront aberrometer images with different spatial frequency peak characteristics. The left hand image in FIG. 9 illustrates a spatial-domain Moiré fringe pattern image whose resulting frequency-domain transformation has peaks that are regularly shaped and have acceptable widths. The right hand image in FIG. 9 illustrates a spatial-domain Moiré fringe pattern image whose resulting frequency-domain transformation has irregularly shaped peaks that are unacceptably wide. The poorly-formed frequency peaks that result from the right hand image can reduce the accuracy of ocular aberration measurement taken from the image. In some embodiments, the width and regularity of spatial frequency peaks are quantified and accounted for in the objective quality metric calculation, for example, as described herein.

Figure 10:
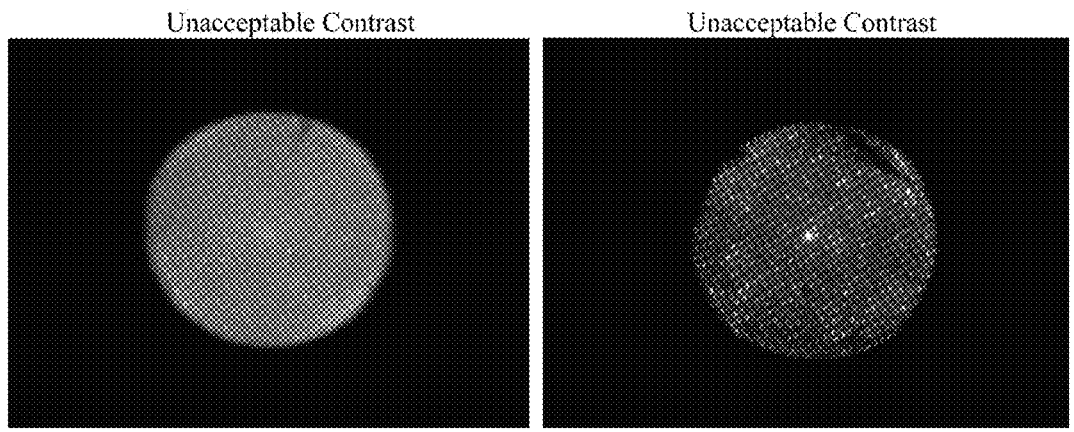
FIG. 10 illustrates two wavefront aberrometer images with unacceptable image contrast.

FIG. 10 illustrates two wavefront aberrometer images with unacceptable image contrast. The image contrast of the left hand image in FIG. 10 suffers as a result of unfiltered ambient light at the operating wavelength of the wavefront aberrometer during an ocular measurement. The image contrast of the right hand image is also unacceptable, but for a different reason. In this case, contrast has suffered as a result of a poor tear film on the patient's eye during the measurement. In either case, the image contrast can be quantified and accounted for in the objective quality metric calculation, for example, as described herein.

Figure 11:
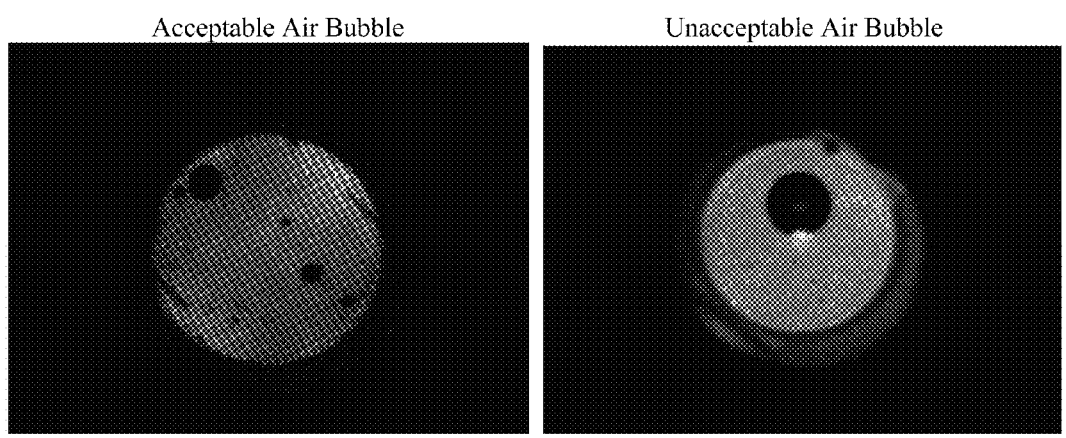
FIG. 11 illustrates two wavefront aberrometer images with air bubbles that obscure a portion of the image.

FIG. 11 illustrates two wavefront aberrometer images with air bubbles that obscure a portion of the image. The left hand image has several relatively small air bubbles that appear within the circular region of the image. Air bubbles of this sort have been found by experimentation to have relatively little negative affect on the accuracy of ocular aberration measurements made from the image. The right hand image has an example of a relatively large air bubble which has been found by experimentation to unacceptably impact the accuracy of ocular aberration measurements. The difference between acceptable air bubbles and unacceptable air bubbles in wavefront aberrometer image data can be subtle. However, the objective quality metric calculations described herein can help differentiate between those images that are unacceptably degraded and those that are not.

Figure 12:
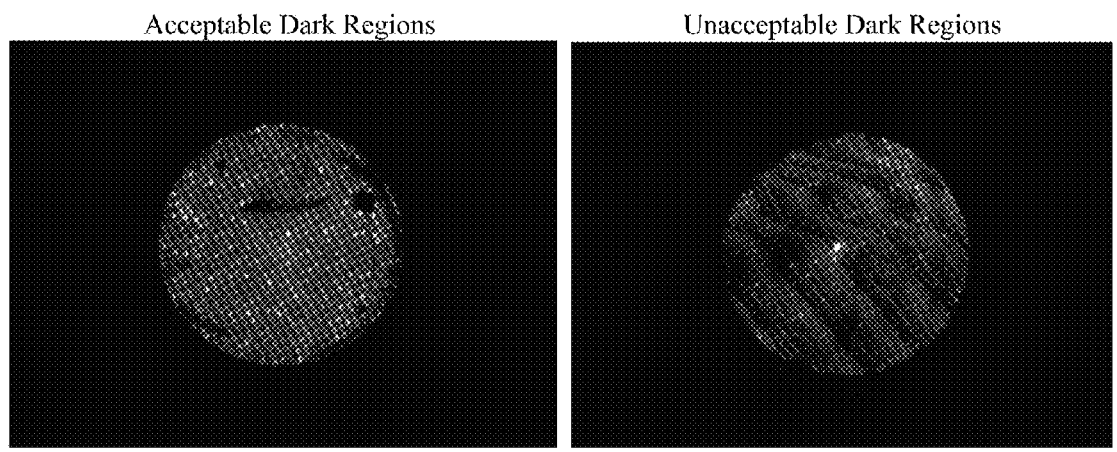
FIG. 12 illustrates two wavefront aberrometer images with dark regions that can affect the accuracy of ocular aberration measurements determined from the images.

FIG. 12 illustrates two wavefront aberrometer images with dark regions that can affect the accuracy of ocular aberration measurements determined from the images. A number of causes can be responsible for dark regions such as those illustrated in FIG. 12, including the cataract, the cortex, etc. The left hand image in FIG. 12 is illustrative of dark regions that have been found to be relatively acceptable in terms of their impact on the accuracy of ocular aberration measurements. The right hand image in FIG. 12, however, illustrates a wavefront aberrometer image with dark regions that unacceptably impact these measurements. Again, the difference between the two cases can be subtle as a matter of degree, making it very advantageous to have objective methods of determining the quality of the image data.

Figure 13:
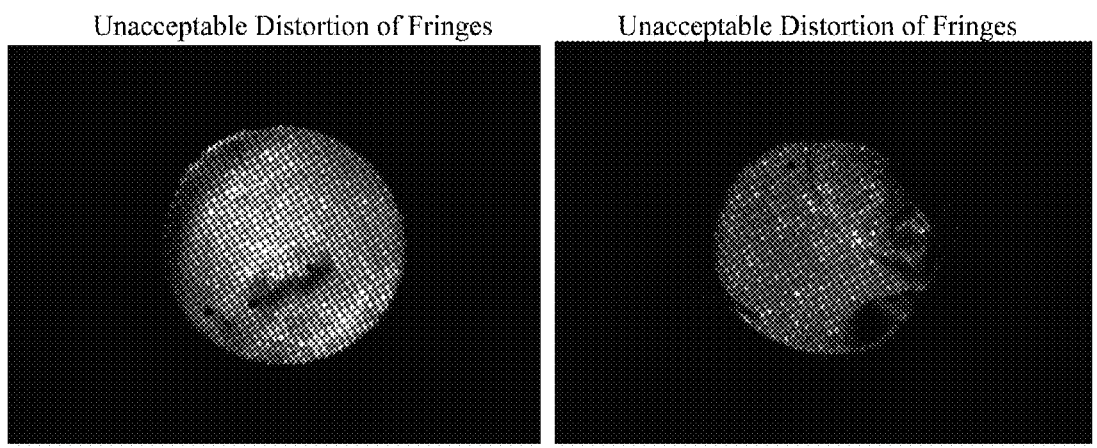
FIG. 13 illustrates two wavefront aberrometer images with an unacceptable amount of distortion in the Moiré fringes.

FIG. 13 illustrates two wavefront aberrometer images with an unacceptable amount of distortion in the Moiré fringes. In certain cases, it is advantageous that the methods described herein are capable of flagging this type of degraded image so that the ocular aberration measurements obtained from them are not used in surgical calculations for determining IOL power in a cataract patient.

Figure 14:
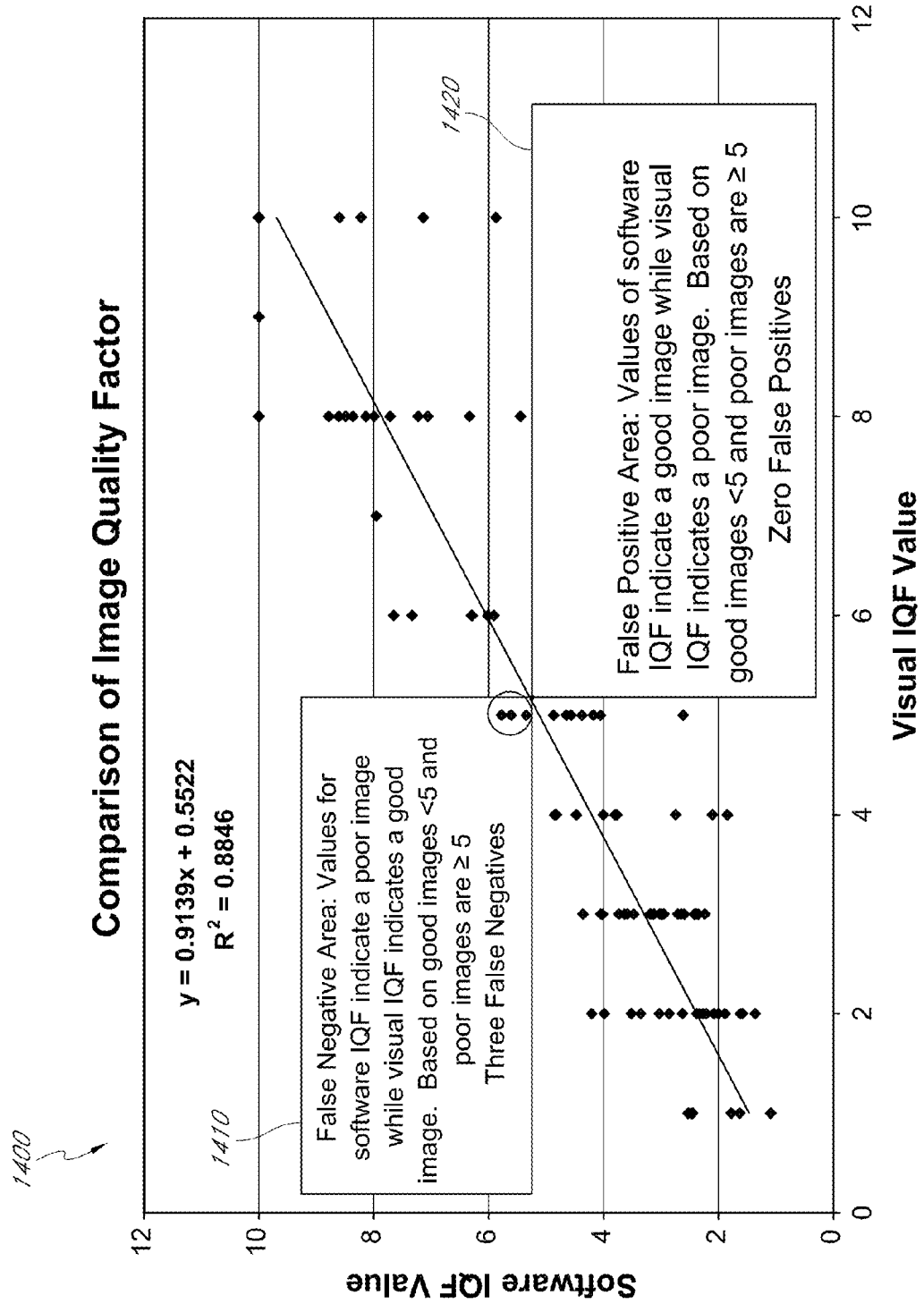
FIG. 14 is a plot 1400 comparing subjective image quality metrics assigned to a test set of wavefront aberrometer image data with machine-generated objective image quality metrics for the same set of test image data.
Figure 15:
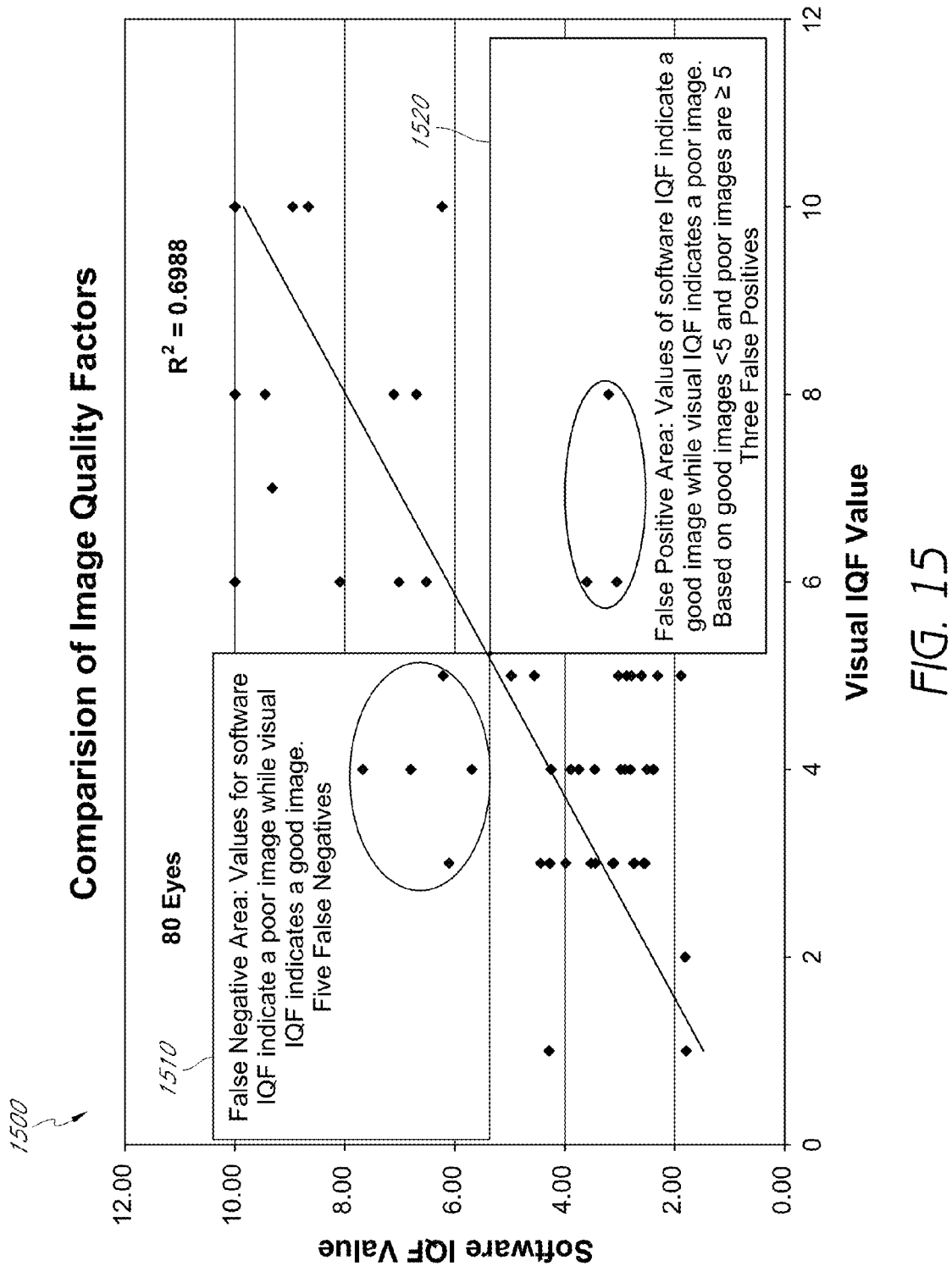
FIG. 15 is a plot 1500 comparing subjective image quality metrics assigned to a non-test set of wavefront aberrometer image data with machine-generated objective image quality metrics for the same set of non-test image data.

FIGS. 14 and 15 illustrate the results of an actual implementation of the equipment and procedures described herein for objectively determining the quality of collected wavefront aberrometer image data. FIG. 14 is a plot 1400 comparing subjective image quality metrics assigned to a training set of wavefront aberrometer image data with machine-generated objective image quality metrics for the same set of training image data. FIG. 14 summarizes the results of examining 60 frames of Moiré fringe pattern images calculated during each of 110 ocular examinations. Each of the images was graded on a scale of 1 to 10 (1 being the highest quality) by careful visual inspection of the human expert. Each of the images was then analyzed using functions $F_n(Y)$ similar to those described herein. The output values of the functions for each image were then averaged (e.g., the amount of decentration for each image was averaged, the respective widths of the primary spectral peaks were averaged, etc.) and used as starting points for the coefficients $C_n$, after which the coefficients were optimized to an acceptable extent based on the subjective scores using a simulated annealing process. An objective quality metric was then calculated for each of the images using the techniques described herein.

FIG. 14 is a scatter plot 1400 of the subjective quality metrics plotted versus the corresponding objective quality metrics. The subjective quality metric is plotted along the horizontal axis, while the objective quality metric is plotted along the vertical axis. A line of best fit for the scatter data was calculated with an $R^2$ value of 0.8846, representing a relatively strong linear correlation between the subjective and objective scores. For purposes of this example, an image with a score ≥5 was counted as a poor image, while those images with a score <5 were counted as good images.

As indicated by the upper left hand box 1410 on the plot, only three images were qualified as "poor" by the machine algorithm when the human expert qualified those images as "good." These three images were false negatives. In this example, there were no instances of false positives where the machine algorithm scored an image as being "good" when the human expert gave a "poor" score, as shown by the lack of points in the lower right hand box 1420.

FIG. 15 is a plot 1500 comparing subjective image quality metrics assigned to a non-training set of wavefront aberrometer image data with machine-generated objective image quality metrics for the same set of non-training image data. In other words, plot 1500 compares the subjective and objective image quality metrics for 80 eyes that were not part of the training data used to determine the coefficients C. As illustrated in the plot 1500, a line of best fit was once again calculated for the coordinate pairs given by plotting the subjective quality metric for each image with the calculated objective quality metric for the image. The $R^2$ value for this case was 0.6988 which was lower than for the training set of image data, but which is to be expected given that the images in this case were not used to calculate the coefficients $C_n$.

The upper left hand box 1510 in plot 1500 illustrates five false negatives where the machine-generated objective quality metric indicated a "poor" image while the human expert judged the image to have "good" quality. The lower right hand box 1520 shows that there were three false positives where the calculated objective quality metric was "good" when the subjective quality metric was "poor." In general, a false negative is preferable to a false positive since it likely only results in the collection of a new set of wavefront aberrometer images, ideally with improved ocular aberration measurement results. The sphere, cylinder, and axis values calculated from the five false negative images were compared with the actual known sphere, cylinder, and axis values for those eyes. The comparison revealed that the measurements obtained from three of the five false negative images were actually outside the range of normal measurement errors, indicating that the machine algorithm had arguably performed better than the human expert in these three cases. In addition, the sphere, cylinder, and axis values calculated from the three false positive images were compared with the actual known measurements for those eyes. In each of the three cases, the measurements calculated from the wavefront aberrometer images fell within the normal range of measurement error when compared with the known values. Once again, this illustrates that the machine algorithm arguably performed better than the human expert since each of the three "false positives" actually yielded accurate ocular aberration measurements.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps may be altered, added, removed, or rearranged in ways that will be appreciated by those of ordinary skill in the art. While certain embodiments have been explicitly described, other embodiments will become apparent to those of ordinary skill in the art based on this disclosure.

The foregoing disclosure has partitioned devices and systems into multiple components or modules for ease of explanation. The components or modules may be embodied as computer hardware (e.g., processors, volatile or non-volatile memories, circuit boards, chipsets, etc.). It is to be understood, however, that one or more components or modules may operate as a single unit. Conversely, a single component or module may comprise one or more sub-components or some-modules. Further, the communication between components or modules may occur in a variety of ways, such as hardware implementations (e.g., over a network, serial interface, parallel interface, or internal bus), software implementations (e.g., database, passing variables), or a combination of hardware and software. Such communications can use a variety of signals, protocols, and standards. In addition, where methods are described that are, or could be, at least in part carried out by computer software, it should be understood that such methods can be provided on computer-readable media (e.g., optical disks such as CDs or DVDs, hard disk drives, flash memories, diskettes, or the like) that, when read by a computer or other processing device, cause it to carry out the method.

The systems and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. In a wavefront aberrometer system, a method comprising:
   obtaining one or more wavefront aberrometer images that are indicative of a patient's ocular aberrations;
   determining a plurality of characteristics of the one or more wavefront aberrometer images;
   determining one or more objective quality metrics for the one or more wavefront aberrometer images, the one or more objective quality metrics being based on an aggregate of the plurality of characteristics of the one or more wavefront aberrometer images;
   selecting at least a portion of the one or more wavefront aberrometer images based on the one or more objective quality metrics; and
   determining one or more ocular aberration measurements using the selected portion of the one or more wavefront aberrometer images.

2. The method of claim 1, further comprising determining a objective quality metric for each of the one or more wavefront aberrometer images.

3. The method of claim 1, further comprising:
   selecting a single wavefront aberrometer image based on one of the one or more objective quality metrics; and
   determining the one or more ocular aberration measurements based on the single selected wavefront aberrometer image.

4. The method of claim 1, wherein the one or more objective quality metrics are calculated using one or more parameters determined from a plurality of training wavefront aberrometer images representative of ocular aberrations.

5. The method of claim 4, wherein the one or more parameters are determined based on subjective quality metrics assigned to the plurality of training wavefront aberrometer images by a human expert.

6. The method of claim 1, wherein determining one or more characteristics of each of the one or more wavefront aberrometer images comprises analyzing a spatial-domain representation of each of the plurality of wavefront aberrometer images.

7. The method of claim 1, wherein determining one or more characteristics of each of the one or more wavefront aberrometer images comprises analyzing a frequency-domain representation of each of the plurality of wavefront aberrometer images.

8. The method of claim 1, wherein the one or more objective quality metrics are quantitative.

9. The method of claim 8, wherein the one or more objective quality metrics are each a scalar value.

10. The method of claim 1, wherein each of the plurality of characteristics is quantified as the output of one or more mathematical functions that each receives one or more of the wavefront aberrometer images as an input.

11. The method of claim 10, wherein each of the one or more objective quality metrics comprises a combination of the outputs of the one or more mathematical functions.

12. The method of claim 11, wherein each of the one or more objective quality metrics comprises a weighted sum of the outputs of the one or more mathematical functions.

13. The method of claim 12, wherein the weightings of the weighted sum are selected based on subjective quality metrics assessed to a plurality of test wavefront aberrometer images by a human expert.

14. The method of claim 13, wherein the weightings of the weighted sum are selected based on the error between one or more objective quality metrics calculated for the plurality of test wavefront aberrometer images and the corresponding one or more subjective quality metrics assessed by the human expert.

15. The method of claim 14, wherein the weightings are selected using a simulated annealing process.

16. The method of claim 1, wherein one of the plurality of characteristics comprises the degree of centration of a feature in each of the one or more images.

17. The method of claim 1, wherein one of the plurality of characteristics comprises the variation in an ocular aberration measurement determined based on each of the one or more wavefront aberrometer images.

18. The method of claim 1, wherein one of the plurality of characteristics comprises the width of a spectral peak identified in a frequency-domain representation of each of the one or more wavefront aberrometer images.

19. The method of claim 18, wherein one of the plurality of characteristics comprises the variation in width of the spectral peak when taken in more than one direction.

20. The method of claim 1, wherein one of the plurality of characteristics comprises the image contrast of a feature of each of the one or more wavefront aberrometer images.

21. The method of claim 20, wherein one of the plurality of characteristics comprises a representative image contrast value determined from a sub-portion of the feature.

22. The method of claim 1, wherein at least one of the one or more wavefront aberrometer images comprises a fringe pattern.

23. The method of claim 22, wherein at least one of the one or more wavefront aberrometer images comprises a Moiré fringe pattern.

24. The method of claim 23, wherein the Moiré fringe pattern comprises a Talbot-Moiré fringe pattern.

25. The method of claim 23, wherein the Moiré fringe pattern comprises a Hartmann-Moiré fringe pattern.

26. The method of claim 1, wherein at least one of the one or more wavefront aberrometer images comprises a Shack-Hartmann spot pattern.

27. The method of claim 1, wherein the one or more ocular aberration measurements comprises the spherical power, the cylindrical power, or the cylindrical axis of the eye.

28. The method of claim 27, further comprising outputting the one or more ocular aberration measurements for use in selecting an intraocular lens to be implanted in the patient's eye during cataract surgery, or for positioning an intraocular lens during cataract surgery.

29. An ophthalmic device, comprising:
   a wavefront aberrometer; and
   a processing module communicatively coupled to the wavefront aberrometer, the processing module being programmed to perform a method comprising,
      obtaining one or more wavefront aberrometer images that are indicative of a patient's ocular aberrations;
      determining a plurality of characteristics of the one or more wavefront aberrometer images;
      determining one or more objective quality metrics for the one or more wavefront aberrometer images, the one or more objective quality metrics being based on an aggregate of the plurality of characteristics of the one or more wavefront aberrometer images;

selecting at least a portion of the one or more wavefront aberrometer images based on the one or more objective quality metrics; and determining one or more ocular aberration measurements using the selected portion of the one or more wavefront aberrometer images.

30. A computer readable medium with instructions that, when read by a computer, cause the computer to perform a method comprising:

obtaining one or more wavefront aberrometer images that are indicative of a patient's ocular aberrations;

determining a plurality of characteristics of the one or more wavefront aberrometer images;

determining one or more objective quality metrics for the one or more wavefront aberrometer images, the one or more objective quality metrics being based on an aggregate of the plurality of characteristics of the one or more wavefront aberrometer images;

selecting at least a portion of the one or more wavefront aberrometer images based on the one or more objective quality metrics; and determining one or more ocular aberration measurements using the selected portion of the one or more wavefront aberrometer images.

\* \* \* \* \*